US011279682B2

(12) United States Patent
de Diego et al.

(10) Patent No.: US 11,279,682 B2
(45) Date of Patent: *Mar. 22, 2022

(54) VORTIOXETINE PYROGLUTAMATE

(71) Applicant: H. Lundbeck A/S, Valby (DK)

(72) Inventors: Heidi Lopez de Diego, Nærum (DK); Kim Lasse Christensen, Slagelse (DK); Rene Holm, Jyllinge (DK); Jens Kateb, Malmö (SE)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,647

(22) Filed: Mar. 6, 2019

(65) Prior Publication Data
US 2019/0210987 A1 Jul. 11, 2019

Related U.S. Application Data

(63) Continuation of application No. 15/152,902, filed on May 12, 2016, now Pat. No. 10,287,261.

(30) Foreign Application Priority Data

May 13, 2015 (DK) .................................. 201500284

(51) Int. Cl.
C07D 295/096 (2006.01)
C07D 207/28 (2006.01)

(52) U.S. Cl.
CPC ....... *C07D 295/096* (2013.01); *C07D 207/28* (2013.01)

(58) Field of Classification Search
CPC .......... A61P 25/18; A61P 25/22; A61P 25/00; A61P 25/24; A61P 25/28; C07D 295/096; C07D 207/28
See application file for complete search history.

(56) References Cited

U.S. PATENT DOCUMENTS

| 4,780,667 A | 12/1988 | Makino et al. |
| 4,789,667 A | 12/1988 | Makino et al. |
| 6,436,946 B1 | 8/2002 | Mann |
| 6,709,678 B2 | 3/2004 | Gruber |
| 8,722,684 B2 | 5/2014 | Bang-Andersen |
| 2011/0201617 A1 | 8/2011 | Moore |

FOREIGN PATENT DOCUMENTS

| GB | 1 006 728 A | 10/1965 |
| WO | WO 94/03186 | 2/1994 |
| WO | 01/76610 A1 | 10/2001 |
| WO | 03/029232 A1 | 4/2003 |
| WO | 2005/107713 A2 | 11/2005 |
| WO | 2005/107713 A3 | 11/2005 |
| WO | 2007/144005 A1 | 12/2007 |
| WO | WO 2010/121621 | 10/2010 |
| WO | 2011/023194 A2 | 3/2011 |
| WO | 2011/023194 A3 | 3/2011 |
| WO | 2011/136376 A1 | 11/2011 |
| WO | 2014/044721 A1 | 3/2014 |
| WO | 2014/128207 A1 | 8/2014 |

OTHER PUBLICATIONS

International Search Report mailed in corresponding international application No. PCT/EP2016/060540 dated Jul. 12, 2016.
Hörter, D. and Dressman, J.B., "Influence of physicochemical properties on dissolution of drugs in the gastrointestinal tract" *Advanced Drug Delivery Reviews* 25:3-14 (1997).
Overgaard, A.B.A., et al., "Patients' evaluation of shape, size and colour of solid dosage forms" *Pharm World Science* 23(5): 185-188 (2001).
Mahableshwarkar, A.R., et al. "A Randomized, Placebo-Controlled, Active-Reference, Double-Blind, Flexible-Dose Study of the Efficacy of Vortioxetine on Cognitive Function in Major Depressive Disorder" *Neuropsychopharmacology* 40:2025-2037 (2015).
McIntyre, R.S., et al., "A randomized, double-blind, placebo-controlled study of vortioxetine on cognitive function in depressed adults" *Int J Neuropsychopharmacology* 17:1557-1567 (2014).
Westrich, L., et al., "In vitro and in vivo effects of the multimodal antidepressant vortioxetine (Lu AA21004) at human and rat targets" *Int. J. Psychiatry Clin Pract.* 15 Suppl 1 p. 47 (2012).
Mørk, A., et al., "Lu AA21004, a novel antidepressant, modulates neurotransmitter levels and theta oscillations, and exerts pro-cognitive effects in rats" *Eur. Neuropshycopharmacol.* 21 (suppl 3) S407-408 (2011).
Moore, N., et al., "Lu AA21004: a novel potential treatment for mood disorders" *Eur. Neuropshycopharmacol.* 18 (suppl 4) S321 (2008).
Bang-Andersen, B., et al., "Discovery of 1-[2-(2,4-Dimethylphenylsulfanyl)phenyl]piperazine (Lu AA21004): A Novel Multimodal Compound for the Treatment of Major Depressive Disorders" *J. Med. Chem.* 54:3206-3221, S1-S45 (2011).
Katona, C., et al., "A randomized, double-blind, placebo-controlled, duloxetine-referenced, fixed-dose study comparing the efficacy and safety of Lu AA21004 in elderly patients with major depressive disorder" *Int. Clin. Psychopharm.* 27:215-221 (2012).
Parrish, "Synthesis and Characterization of Polymeric Materials Derived from 2,5-Diketopiperazines and Pyroglutamic Acid", https://aquila.usm.edu/theses_dissertations/2382, Jan. 8, 2018.
Supplementary material—list of pharmaceutically acceptable acids, Based on Handbook of Pharmaceutical Salts, excluding polymers, Electronic Supplementary Material for CrystEngComm, This Journal is © The Royal Society of Chemistry 2005.
Parrish et al., "Supramolecular Materials from Multifunctional Pyroglumatic Acid Derivatives", Macromolecules, 36, pp. 4250-4252, 2003.
Smith et al., "Methacrylate Derivatives Incorporating Pyroglutamic Acid", Biomacramolecules, 3, pp. 1392-1399, 2002.

(Continued)

*Primary Examiner* — Lezah Roberts

(74) *Attorney, Agent, or Firm* — Fish & Richardson P.C.

(57) ABSTRACT

The present invention provides vortioxetine pyroglutamate salt and pharmaceutical compositions comprising said salt.

10 Claims, 14 Drawing Sheets

(56) References Cited

OTHER PUBLICATIONS

Figure 1:
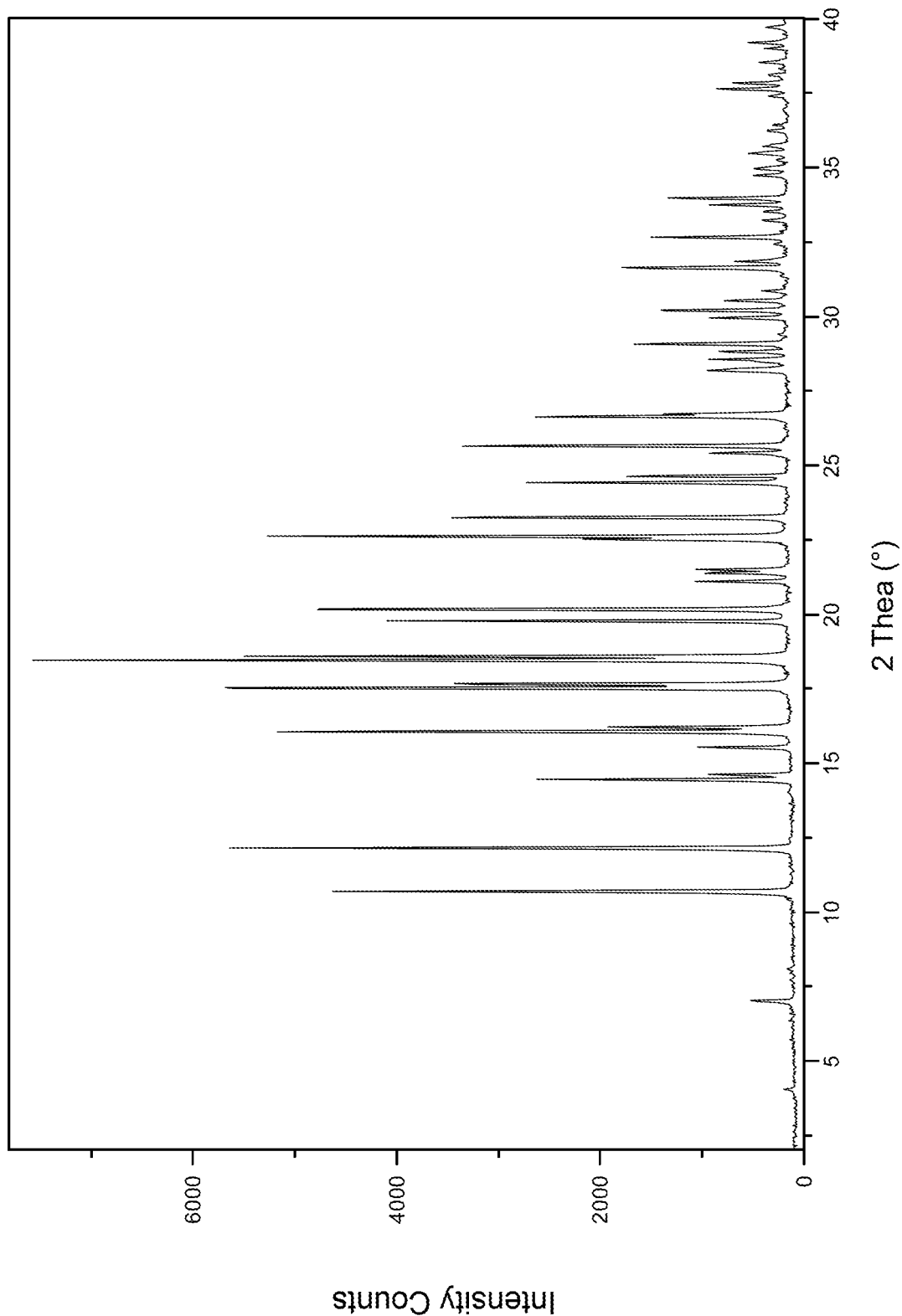

Järvinen et al., "Enteric Coating Reduces Upper Gastrointestinal Adverse Reactions to Doxycycline", Clin. Drug Invest. 10 (6), pp. 323-327, 1995.
Mena et al., Formation of Extracellular Glutamate from Glutamine: exclusion of Pyroglutamate as an Intermediate, Bran Research, vol. 1052, No. 1, Aug. 2, 2005, pp. 88-96.
Blier, P., et al., "Is There a Role for 5-$HT_{1A}$ Agonists in the Treatment of Depression?" *Society of Biological Psychiatry* 53:193-203 (2003).
Hindle, A. T., "5HT3 Receptor Antagonists," *Current Anaesthesia and Critical Care* 6:242-249 (1995).

VORTIOXETINE PYROGLUTAMATE

CROSS REFERENCE TO RELATED APPLICATIONS

This application is a continuation of U.S. application Ser. No. 15/152,902, filed May 12, 2016, which claims priority to Danish Application No. PA201500284, filed May 13, 2015. The contents of the parent applications are hereby incorporated by reference in their entirety.

TECHNICAL FIELD

The present invention relates to vortioxetine pyroglutamate and its use in pharmaceutical compositions.

BACKGROUND

International patent applications including WO 03/029232 and WO 2007/144005 disclose the compound 1-[2-(2,4-dimethyl-phenylsulfanyl)-phenyl]-piperazine and pharmaceutically acceptable salts thereof. WHO has since published that vortioxetine is the recommended International Non-proprietary Name (INN) for 1-[2-(2,4-dimethyl-phenylsulfanyl)-phenyl]-piperazine. Vortioxetine was formerly referred to in the literature as Lu AA21004. In September and December 2013 FDA and EMA, respectively, approved vortioxetine for the treatment of major depressive disorder/major depressive episode under the trade name Brintellix™. Of particular interest, vortioxetine has also shown effect in elderly suffering from recurrent major depressive disorder [*Int. Clin. Psychopharm.*, 27, 215-227, 2012].

Vortioxetine is an antagonist on the $5-HT_3$, $5-HT_7$ and $5-HT_{1D}$ receptors, an agonist on the $5-HT_{1A}$ receptor and a partial agonist on the $5-HT_B$ receptor and an inhibitor of the serotonin transporter. Additionally, vortioxetine has demonstrated to enhance the levels of the neurotransmitters serotonin, noradrenalin, dopamine, acetylcholine and histamine in specific areas of the brain. All of these activities are considered to be of clinical relevance and potentially involved in the mechanism of action of the compound [*J. Med. Chem.*, 54, 3206-3221, 2011; *Eur. Neuropshycophar-macol.*, 18(suppl 4), S321, 2008; *Eur. Neuropshycopharma-col.*, 21(suppl 4), S407-408, 2011; *Int. J. Psychiatry Clin Pract.* 5, 47, 2012]. The pharmacological profile gives reason to believe that vortioxetine may have a pro-cognitive effect. This notion seems to be supported by clinical evidence where vortioxetine has been shown to have a direct beneficial effect on cognition independent of its antidepressive effects [*Int. Clin. Psychopharm.*, 27, 215-227, 2012; *Int J neurophychopharm* 17, 1557-1567, 2014; *Neuropsycho-pharmacol*, 40, 2025-2037, 2015.

Vortioxetine is available on the market as film coated instant release (IR) tablets containing 5, 10, 15 and 20 mg vortioxetine as the HBr salt and as an oral drop solution comprising 20 mg/ml vortioxetine as the DL lactate salt.

It is well-established that swallowing tablets and capsules may be a problem for a significant number of patients, and this may ultimately lead to lack of compliance with the consequent increased risk of inadequate treatment response or relapse. Studies have shown that every third woman and every sixth man report problems with swallowing tablets. Notably, difficulties with swallowing tablets seem to be more wide-spread in the elderly population and amongst children [*Pharm World Sci*, 23, 185-188, 2001]. Different technologies have been applied to overcome the problems with swallowing tablets and capsules. For example, alternatives to oral administration may be used, such as parenteral, transdermal, nasal, buccal, sublingual or rectal administration. Alternatively, easy-to-swallow oral administration forms such as oral solutions, oral dispersible tablets, powders or granules to be sprinkled on food or oral gels may be applied.

Gel compositions for oral administration are an attractive alternative to tablets and capsules because they combine the ease and simplicity of oral administration with little or no resistance to swallowing. Due to the inherent decreased stability of pharmaceutical products in liquid or semi-solid (e.g. gel form) compositions, gel compositions are often provided as dry powders which are to be mixed with a liquid, typically water or saliva, immediately prior to use to form the gel. U.S. Pat. No. 6,709,678 discloses a pharmaceutical composition comprising an active ingredient in combination with hydratable polymers, such as alginates or carboxymethylcellulose which upon contact with saliva forms a gel in the mouth. WO 01/76610 discloses a composition comprising vitamin D and starch derivatives which upon mixing with water forms a pudding-like gelled suspension. WO 2005/107713 discloses a composition comprising an active ingredient together with gellan gum which upon addition of water swells or gels to have a texture similar to that of a soft pudding. Such administration form has been developed for commercial use under the trade name Parvulet™. Parvulet™ comes as a spoon preloaded with active ingredient and a gelling polymer and wrapped in foil. The user unwraps the spoon and adds water to form the gel. It is a common characteristic of these technologies that gelling or swelling is obtained by use of gelling polymers. The application of additional excipients in any pharmaceutical composition is always problematic because it increases the risk of lack of compatibility between the active ingredient and the excipients or between excipients.

One aim of the present invention is to provide vortioxetine salts which can be administered as an oral gel without the need for gelling polymers.

WO 2011/023194 and WO 2011/136376 disclose enteric coated (EC) formulations comprising vortioxetine. One aim of the present invention is to provide enteric coated formulations with superior pharmacokinetic properties.

SUMMARY OF THE INVENTION

The present inventors have surprisingly found that a particular acid addition salt of vortioxetine, namely vortioxetine pyroglutamate in its various forms in aqueous solution forms a gel in the presence of a salt. Accordingly, in one embodiment, the invention relates to vortioxetine pyroglutamate.

In one embodiment, the invention relates to vortioxetine pyroglutamate for use in therapy.

In one embodiment, the invention relates to a pharmaceutical composition comprising vortioxetine pyroglutamate.

In one embodiment, the invention relates to a gel composition comprising vortioxetine pyroglutamate, a salt and water.

In one embodiment, the invention relates to a method for preparing a gel said method comprising the steps of mixing vortioxetine pyroglutamate, a salt and an aqueous solution.

In one embodiment, the invention relates to the use of vortioxetine pyroglutamate in the manufacture of a medicament for the treatment of a CNS disease.

In one embodiment, the invention relates to vortioxetine pyroglutamate for use in a method for the treatment of a CNS disease.

In one embodiment, the invention relates to a method for treating a CNS disease, the method comprising administering a therapeutically effective amount of vortioxetine pyroglutamate to a patient in need thereof.

In one embodiment, the invention relates to a method for treating a CNS disease, the method comprising administering a therapeutically effective amount of a gel composition of the present invention to a patient in need thereof.

FIGURES

FIG. 1: X-ray Powder Diffraction (XRPD) spectrum of vortioxetine (L)-pyroglutamate.

Figure 2:
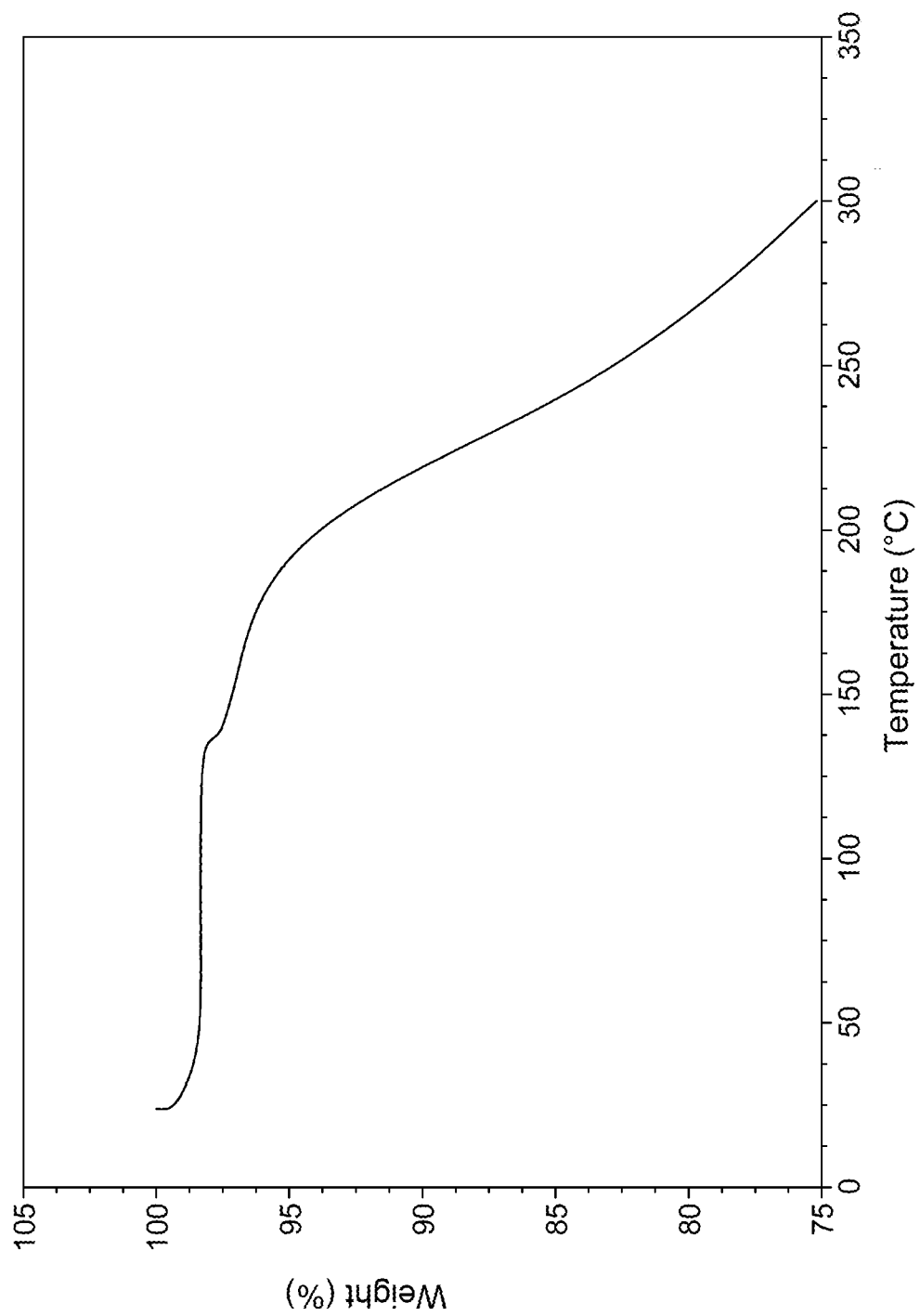

FIG. 2: Thermogravimetric Analysis (TGA) thermogram of vortioxetine (L)-pyroglutamate.

Figure 3:
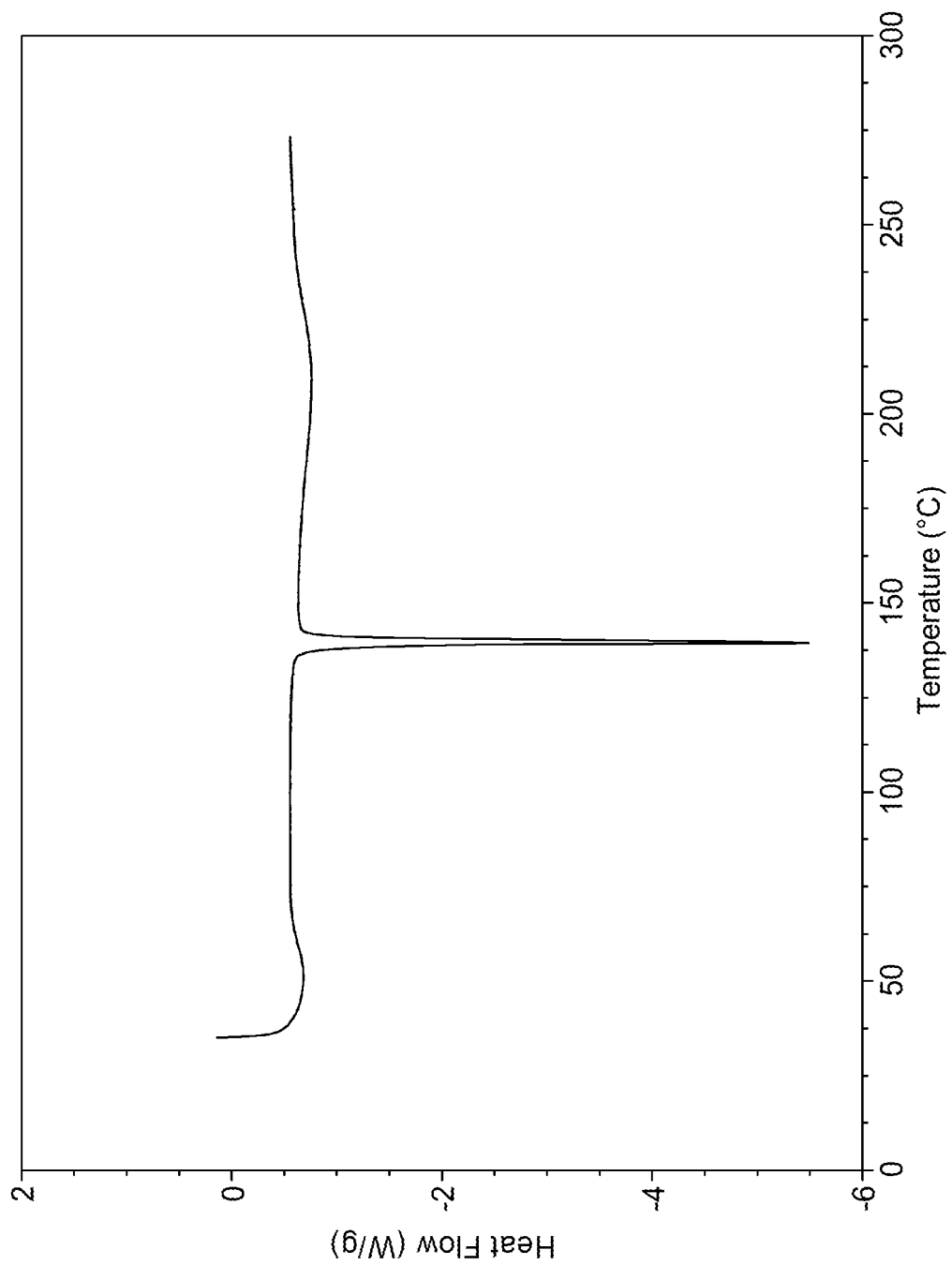

FIG. 3: Differential Scanning Calorimetry (DOS) of vortioxetine (L)-pyroglutamate.

Figure 4:
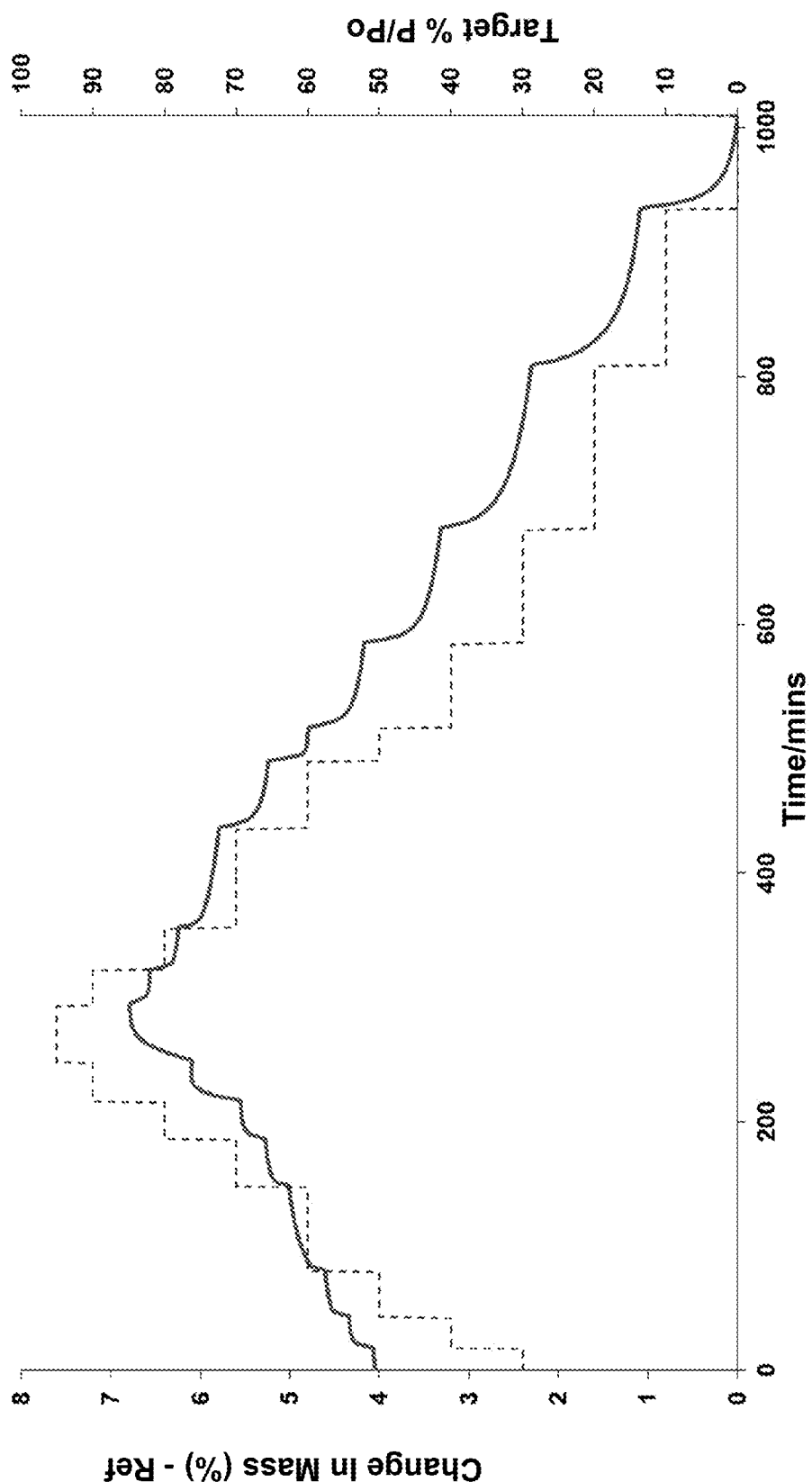

FIG. 4: Dynamic Vapour Sorption (DVS) spectrum for vortioxetine (L)-pyroglutamate. (- - - - - - - - - - -): Change in mass (%) relative to dry state. (— — —) Target relative humidity (%).

Figure 5:
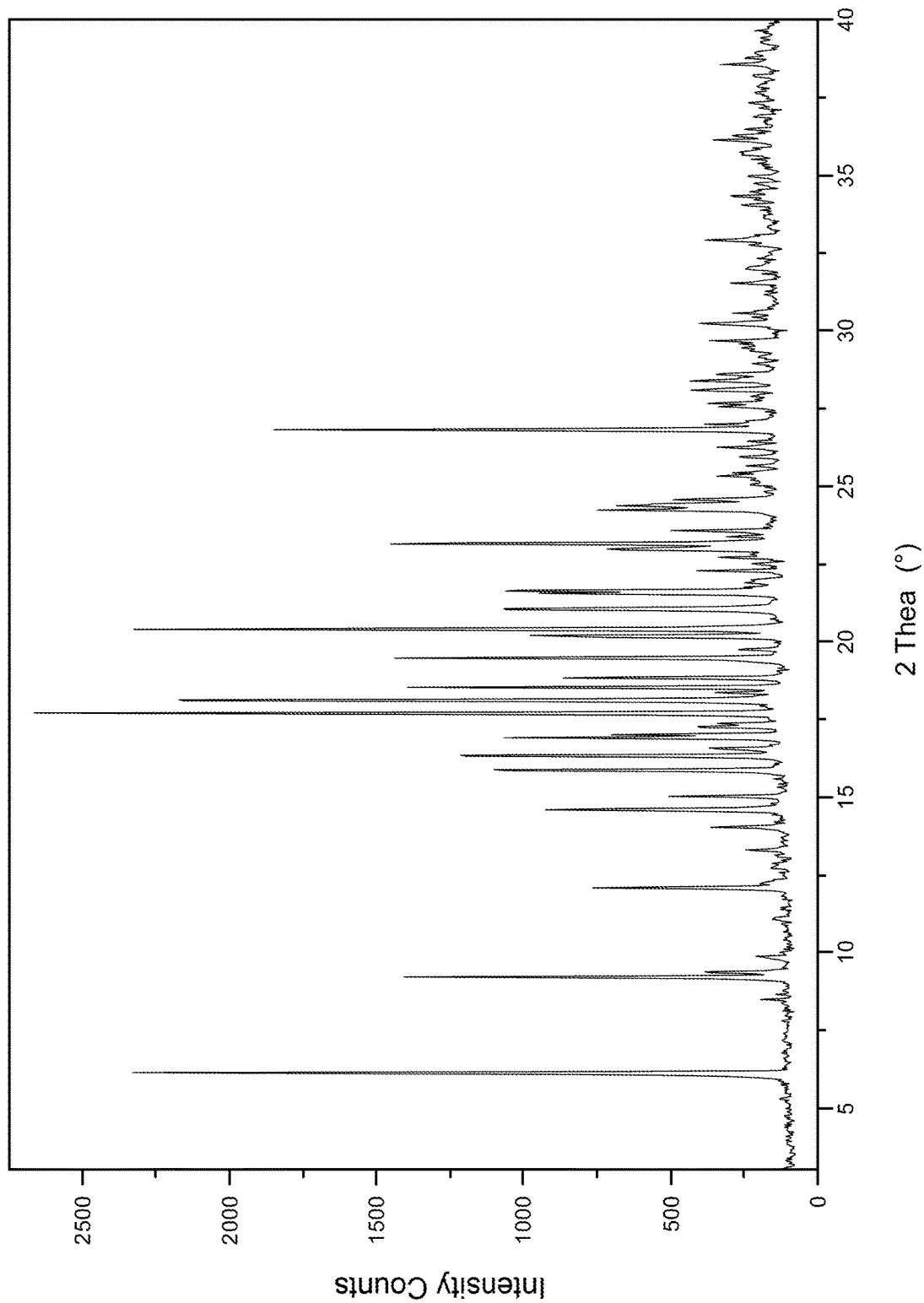

FIG. 5: X-ray Powder Diffraction spectrum of vortioxetine (DL)-pyroglutamate MH.

Figure 6:
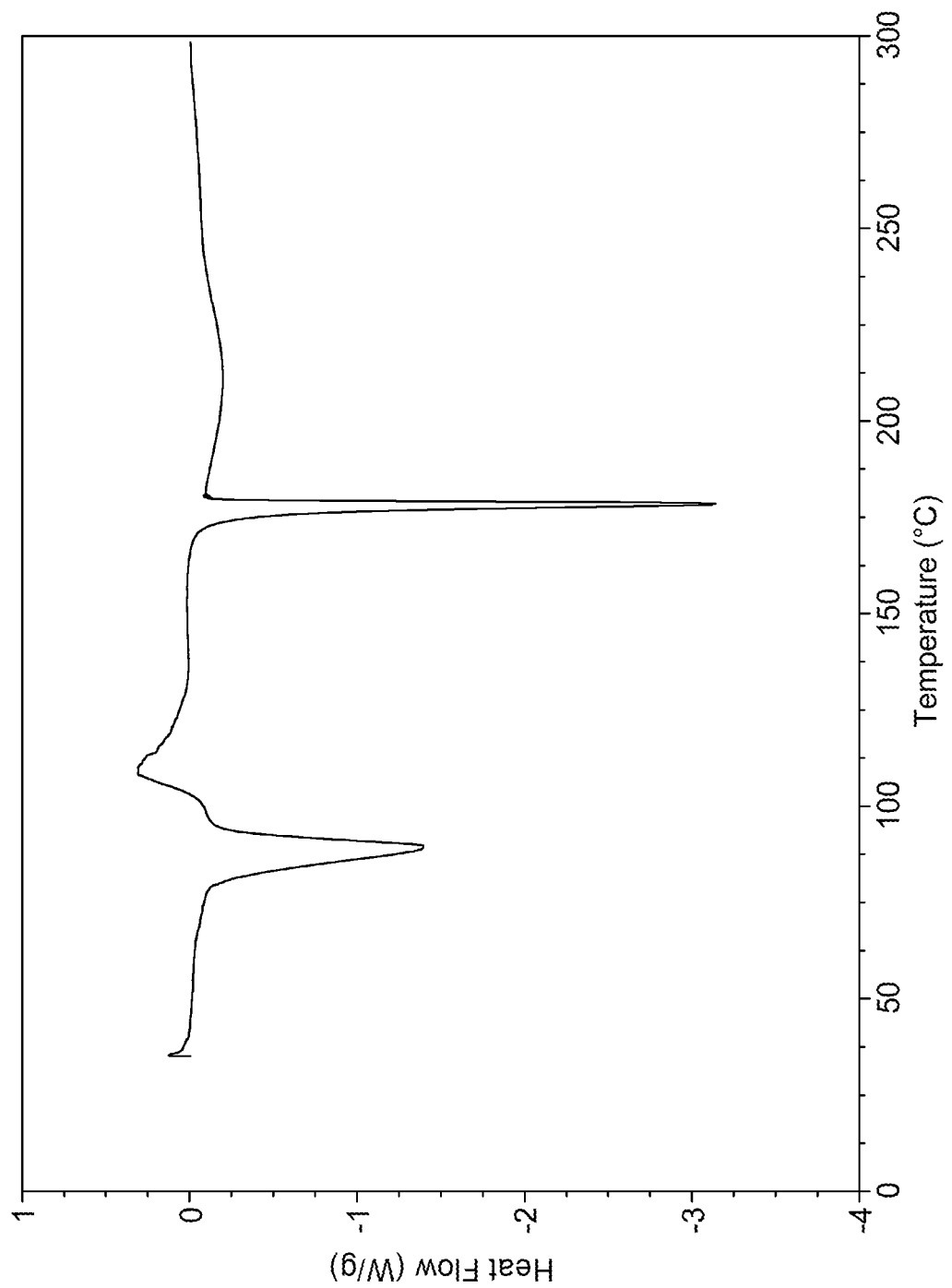

FIG. 6: Differential Scanning calorimetry of vortioxetine (DL)-pyroglutamate MH.

Figure 7:
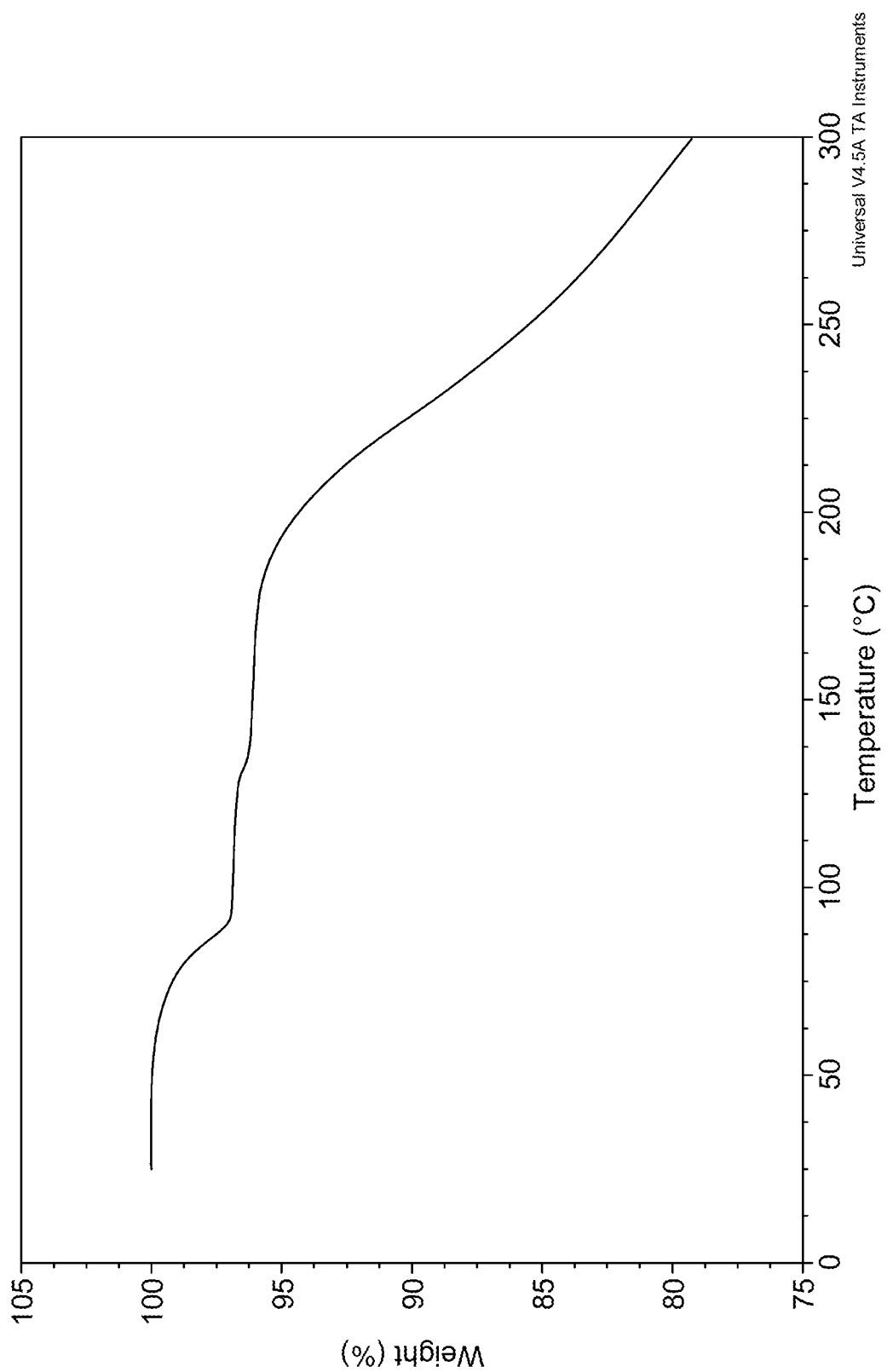

FIG. 7: Thermogravimetric Analysis thermogram of vortioxetine (DL)-pyroglutamate MH.

Figure 8:
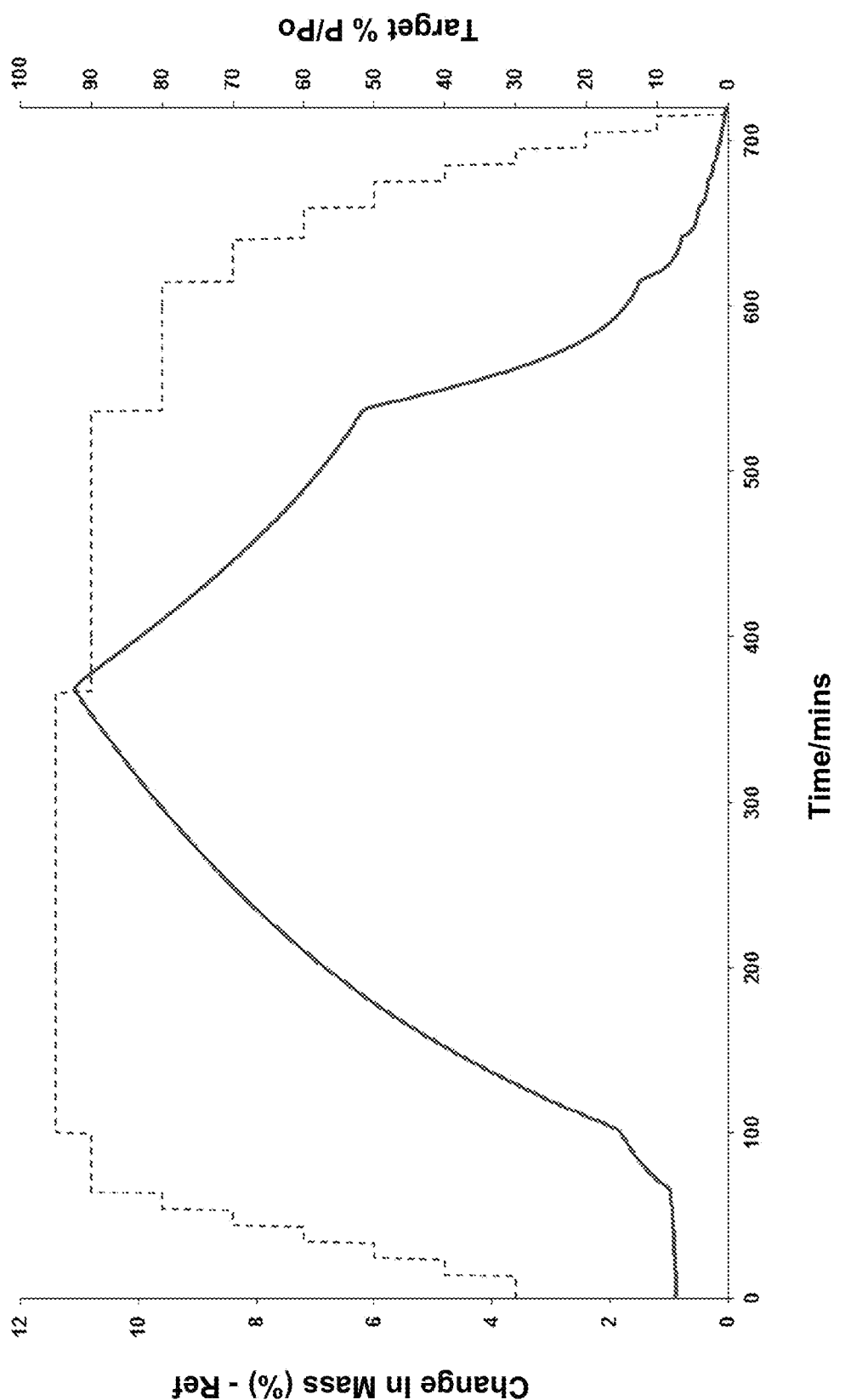

FIG. 8: Dynamic Vapour Sorption spectrum for vortioxetine (DL)-pyroglutamate MH. (- - - - - - - - - - -): Change in mass (%) relative to dry state. (— — —) Target relative humidity (%).

Figure 9:
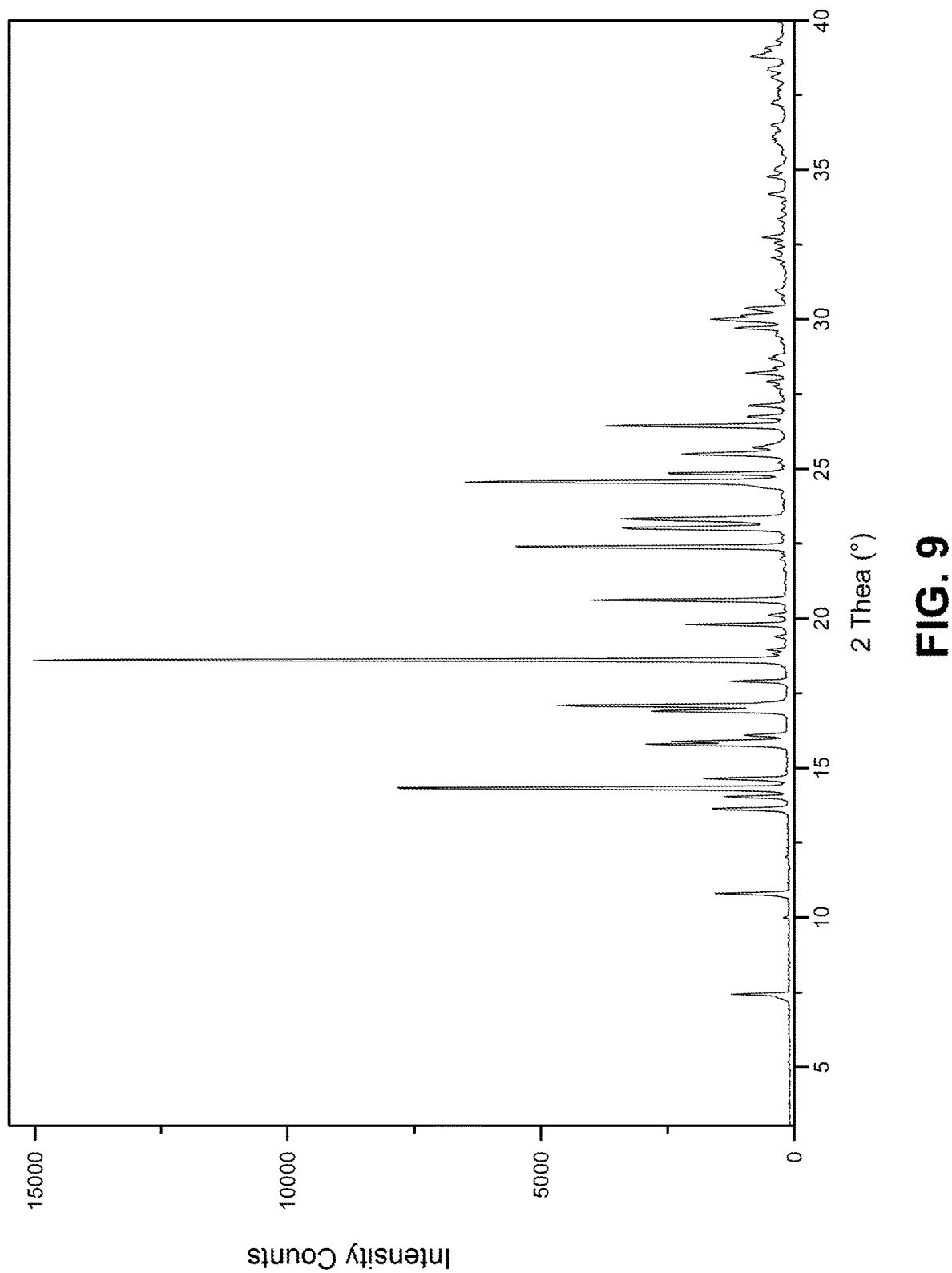

FIG. 9: X-ray Powder Diffraction spectrum of vortioxetine (DL)-pyroglutamate α-form.

Figure 10:
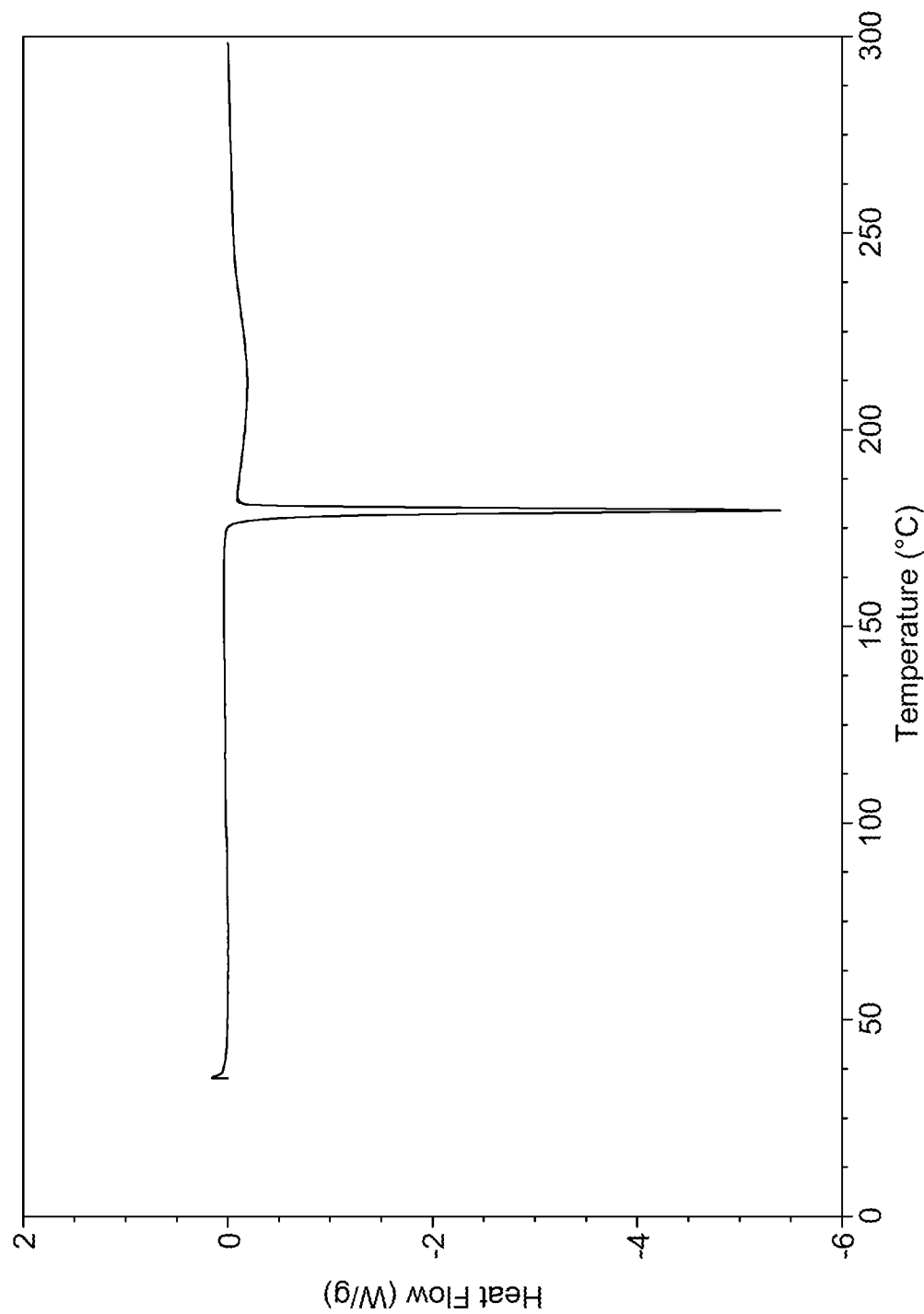

FIG. 10: Differential Scanning calorimetry of vortioxetine (DL)-pyroglutamate α-form.

Figure 11:
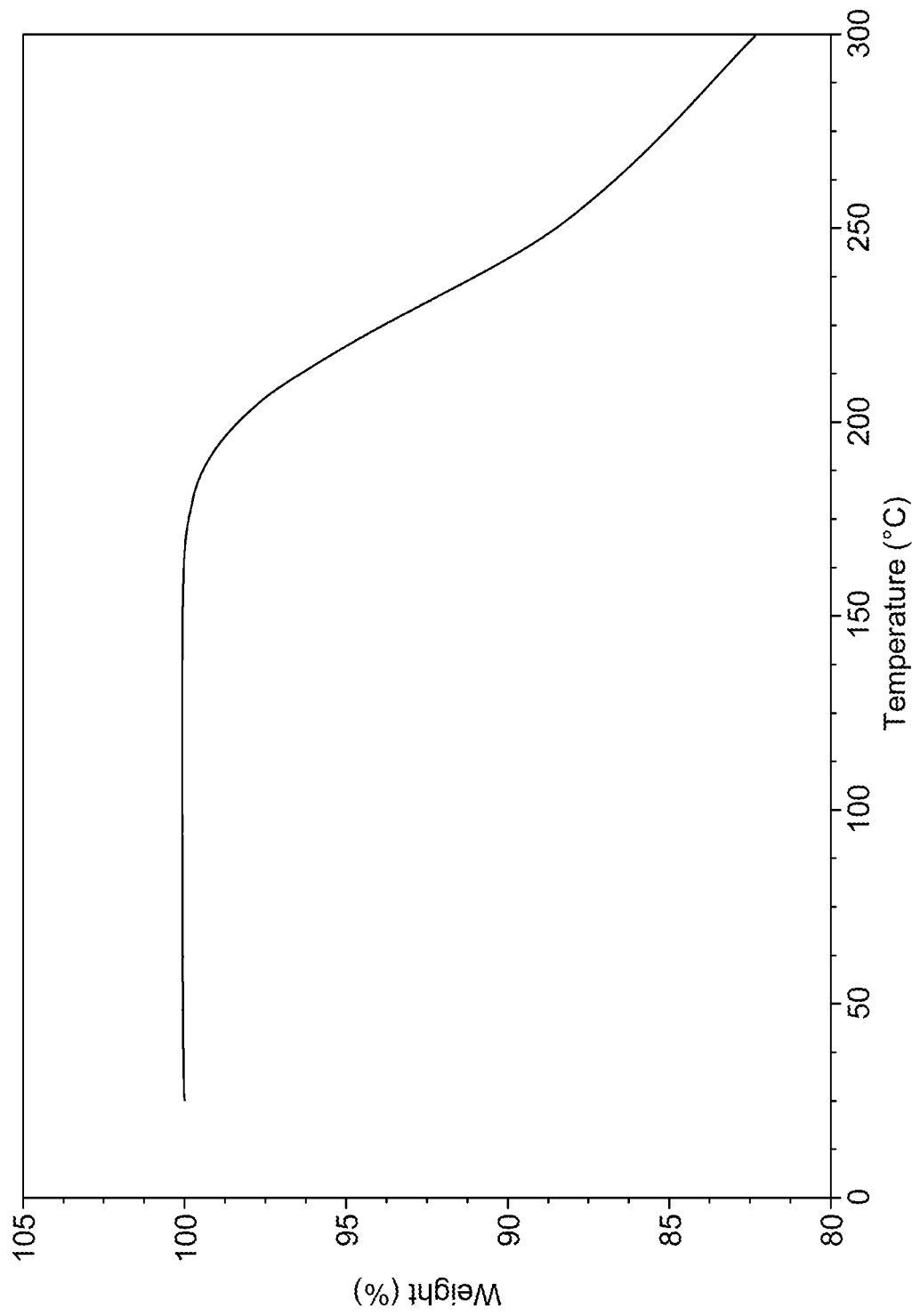

FIG. 11: Thermogravimetric Analysis thermogram of vortioxetine (DL)-pyroglutamate α-form.

Figure 12:
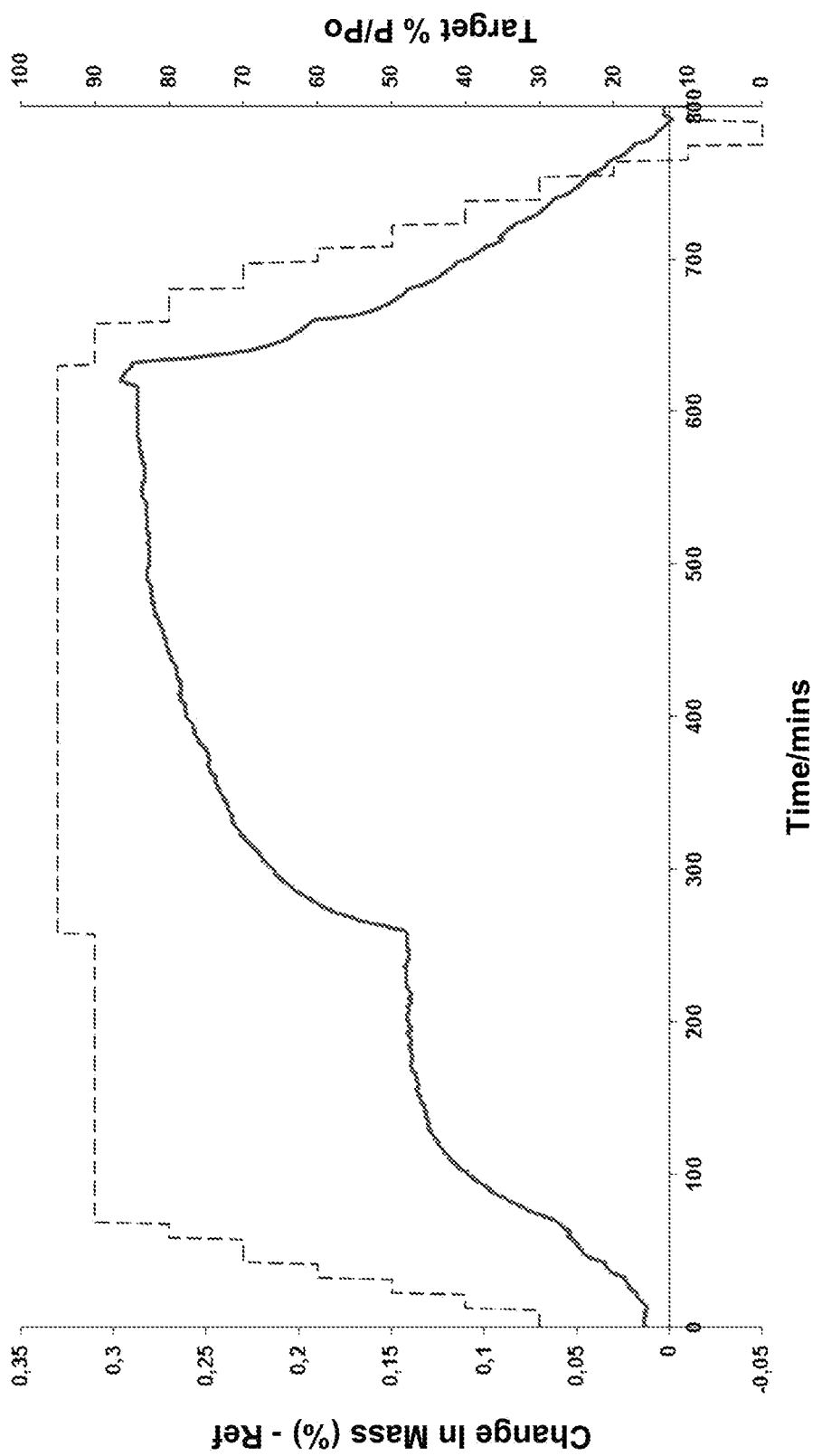

FIG. 12: Dynamic Vapour Sorption spectrum for vortioxetine (DL)-pyroglutamate α-form. (- - - - - - - - - - -): Change in mass (%) relative to dry state. (— — —): Target relative humidity (%).

Figure 13:
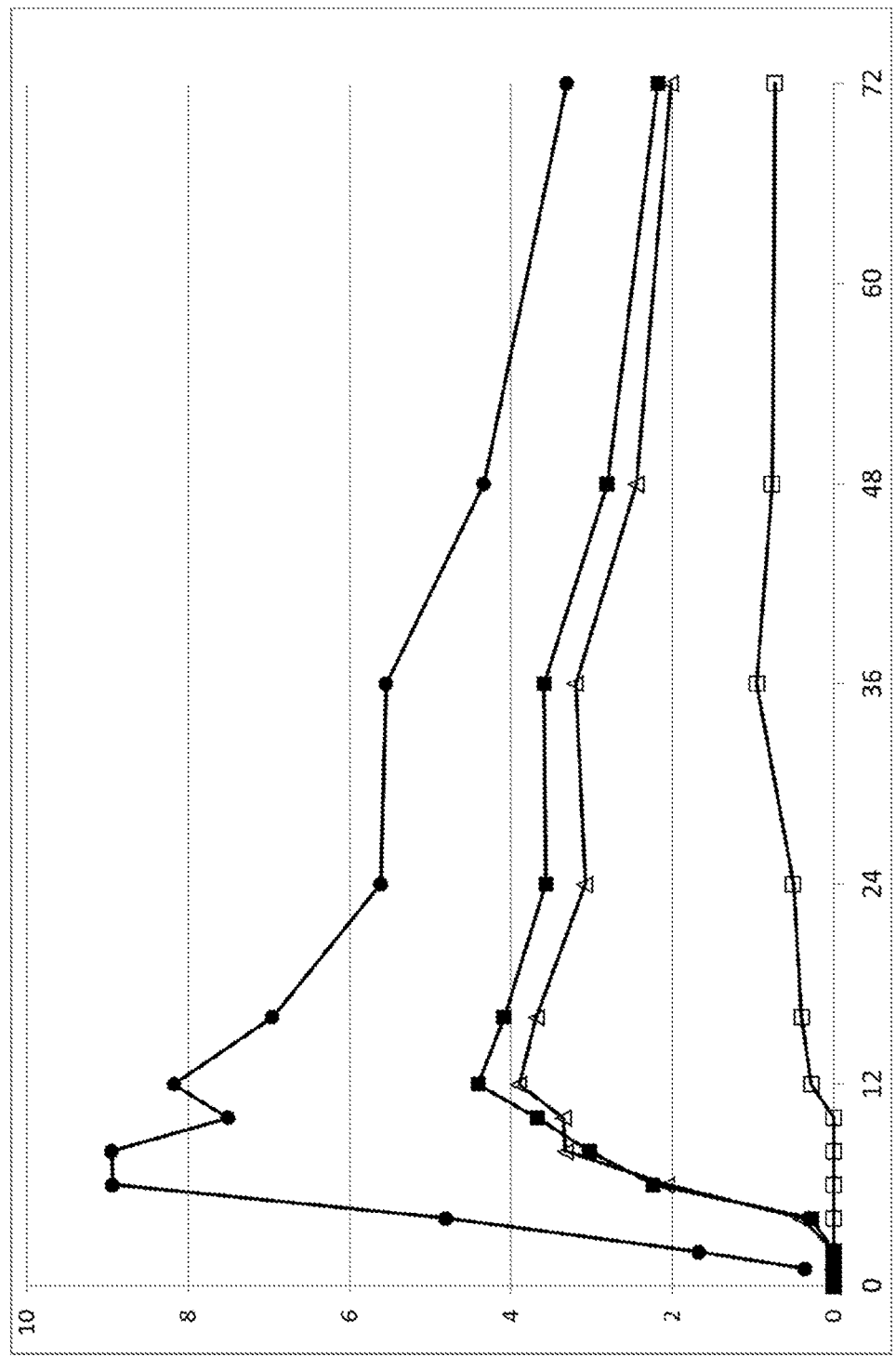

FIG. 13: Plasma concentration-time profiles for vortioxetine in human. X-axis is time in hours post-dosing. Y-axis is plasma concentration in ng/ml. ●IR (20 mg); Δ pH 5.5 (20 mg); ■pH 6.0 (20 mg); pH 7.0 (20 mg)

Figure 14:
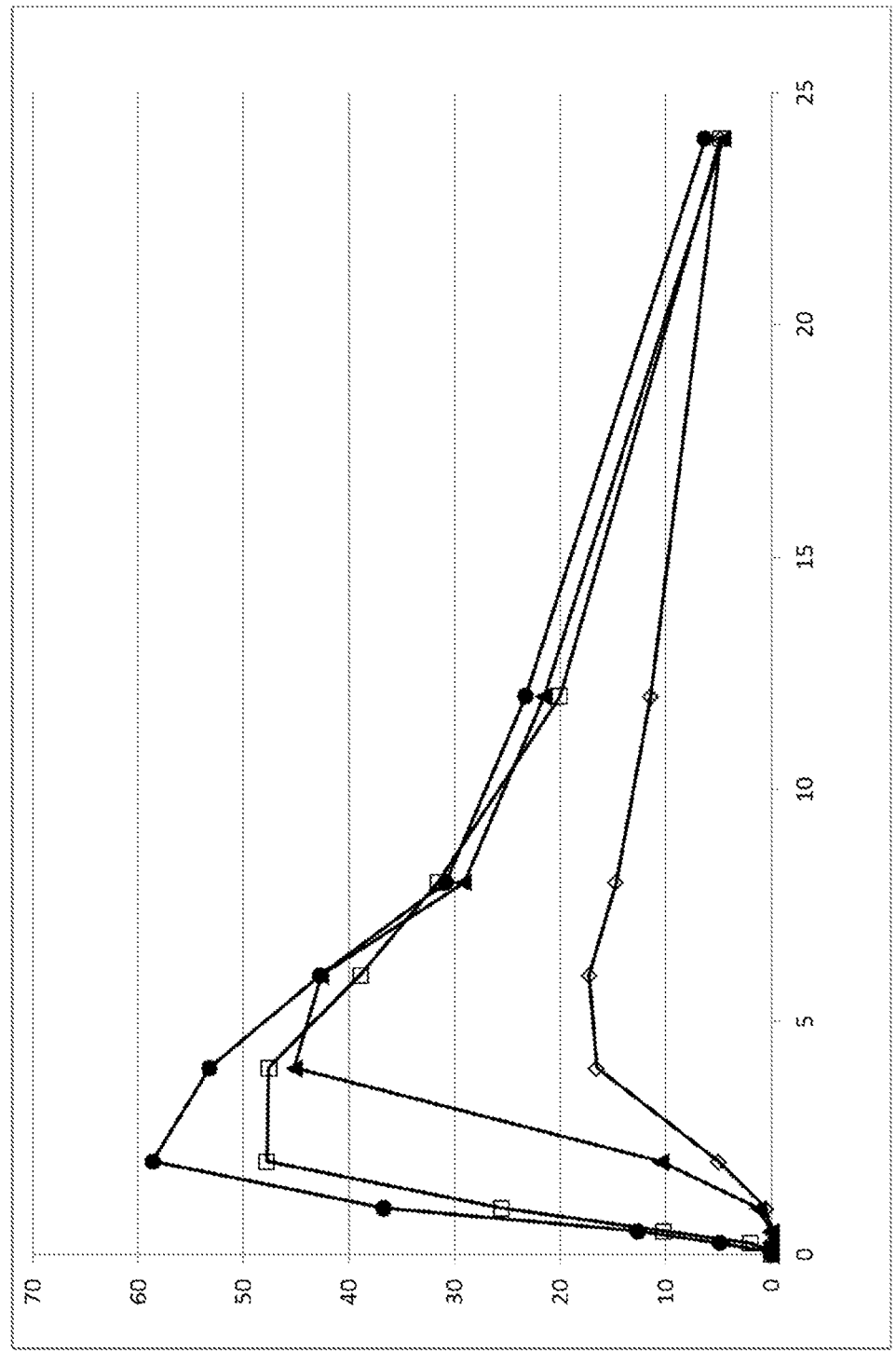

FIG. 14: Plasma-concentration profiles for vortioxetine in dogs. X-axis is time in hours post-dosing. Y-axis is plasma concentration in ng/ml. ●20 mg solution; ◇ 20 mg EC HBr, 20 mg IR HBr; ▲20 mg EC pyroglutamate.

DETAILED DESCRIPTION OF THE INVENTION

The present invention relates to pyroglutamate salts of vortioxetine. Vortioxetine is commercially available or can be synthesised as disclosed in e.g. WO 03/029232, WO 2007/144005 or WO 2014/128207. The molecular structure of vortioxetine is depicted below.

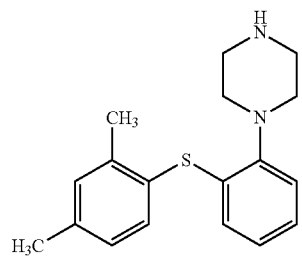 [SMILES: Cc1ccc(Sc2ccccc2N2CCNCC2)c(C)c1]

The pyroglutamate salts of the present invention may be obtained in a reaction between vortioxetine free base and pyroglutamic acid followed by precipitation, as shown in the examples.

Pyroglutamic acid, which is also known as 5-oxoproline and pidolic acid, is formed when the amino group and the side-chain carboxylic acid of glutamic acid cyclize to form a lactam, as shown in the figure below

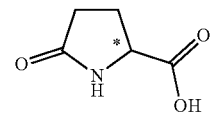

As indicated by the *, pyroglutamate contains an asymmetric carbon atom and pyroglutamate therefore exists in three forms, i.e. DL (the racemic form) and D and L (the two enantiomeric) forms. The physical properties of vortioxetine pyroglutamate salts may in principle depend on whether the counter ion is pyroglutamate in its racemic form or either of its enantiomeric forms. However, as shown in the examples, both DL-pyroglutamate and L-pyroglutamate vortioxetine salts can form the gel compositions of the present invention. Since vortioxetine itself does not contain an asymmetric carbon atom and therefore does not exist in enantiomeric forms, vortioxetine L-pyroglutamate and vortioxetine D-pyroglutamate have identical physical properties, including the gelling properties observed by the inventors. Therefore, the invention provides vortioxetine pyroglutamate and uses thereof as described herein wherein pyroglutamate is DL-pyroglutamate, D-pyroglutamate or L-pyroglutamate or any mixture thereof.

Both DL- and L-pyroglutamic acid form 1:1 salt with vortioxetine. As evidenced by the XRPD reflections shown in the examples, these salts are crystalline and both hydrated and anhydrous forms exist. However, as vortioxetine pyroglutamate is dissolved prior to or as part of the gel formation, the gel-forming property of vortioxetine pyroglutamate is unlikely to depend on a particular crystalline form of vortioxetine pyroglutamate.

In one embodiment, the invention relates to vortioxetine D-pyroglutamate or L-pyroglutamate with XRPD reflections at 10.72, 12.14, 16.22 and 18.59 (°2θ); such as 10.72, 12.14, 16.05, 16.22, 17.53, 17.70, 18.45 and 18.59 (°2θ), such as 7.02, 10.72, 12.14, 14.45, 14.61, 15.56, 16.05, 16.22, 17.53, 17.70, 18.45 and 18.59 (°2θ). All values are ±0.1°2θ. In one embodiment, the invention relates to vortioxetine D-pyroglutamate or L-pyroglutamate with XRPD reflection as shown in FIG. 1.

In one embodiment, the invention relates to vortioxetine (DL)-pyroglutamate MH (i.e. MonoHydrate) with XRPD reflections at 6.16, 9.25, 17.68 and 18.12 (°2θ), such as at 6.16, 9.25, 14.61, 15.02, 15.88, 16.33, 17.68 and 18.12

(°2θ), such as at 6.16, 9.25, 9.38, 12.10, 14.03, 14.61, 15.02, 15.88, 16.33, 16.91, 17.68 and 18.12 (°2θ). All values are ±0.1°2θ. In one embodiment, the invention relates to vortioxetine (DL)-pyroglutamate MH with XRPD reflection as shown in FIG. 5.

In one embodiment, the invention relates to vortioxetine (DL)-pyroglutamate α-form with XRPD reflections at 14.27, 15.75, 17.06 and 18.59 (°2θ), such as at 7.42, 10.78, 13.58, 14.27, 14.60, 15.75, 17.06 and 18.59 (°2θ), such as at 7.42, 10.78, 13.58, 13.99, 14.27, 14.60, 15.75, 15.90, 16.89, 17.06, 17.87 and 18.59 (°2θ). All values are ±0.1°2θ. In one embodiment, the invention relates to vortioxetine (DL)-pyroglutamate α-form with XRPD reflection as shown in FIG. 9.

As shown in the examples, the aqueous solubility of vortioxetine pyroglutamate is markedly higher than that of any known vortioxetine salt. The solubility of vortioxetine DL-pyroglutamate MH and vortioxetine DL-pyroglutamate α-form is at least 278 mg/ml, and solubility of vortioxetine D-pyroglutamate or vortioxetine L-pyroglutamate is 225 mg/ml. These solubility values are determined in water at approximately 20° C. This is to be compared with solubility data for known vortioxetine salts as depicted in the table below:

| Salt | Solubility (mg/ml) | Reference |
| --- | --- | --- |
| Free base | 0.1 | WO 2007/144005 |
| HBr α-form | 2 | WO 2007/144005 |
| HBr β-form | 1.2 | WO 2007/144005 |
| HBr γ-form | NA | WO 2007/144005 |
| HBr hydrate | NA | WO 2007/144005 |
| HBr ethyl acetate solvate | NA | WO 2007/144005 |
| HCl | 3 | WO 2007/144005 |
| HCl mono hydrate | 2 | WO 2007/144005 |
| Mesylate | >45 | WO 2007/144005 |
| Fumerate | 0.4 | WO 2007/144005 |
| Maleate | 1 | WO 2007/144005 |
| Meso-tartrate | 0.7 | WO 2007/144005 |
| L-tartrate | 0.4 | WO 2007/144005 |
| D-tartrate | 0.4 | WO 2007/144005 |
| Sulphate | 0.1 | WO 2007/144005 |
| Phosphate | 1 | WO 2007/144005 |
| Nitrate | 0.8 | WO 2007/144005 |
| HBr with XRPD reflections at 5.5, 14.8, 16.7 and 20.0 (°2θ) | 3-3.8 (Calculated) | WO 2014/044721 |
| L-lactate Monohydrate2 | 26 | WO 2010/121621 |
| DL-lactate β-form | 8 | WO 2010/121621 |

It is evident that vortioxetine pyroglutamate has unparalleled solubility which is ~5 times more soluble than the second most soluble salt (mesylate) and ~200 and ~25 times more soluble than the marketed salts (HBr and DL-lactate). This high solubility is beneficial if vortioxetine is to be administered or sold in e.g. liquid formulations at high concentrations, such as infusion concentrates and oral drops.

In one embodiment, the invention relates to vortioxetine pyroglutamate for use in therapy.

In one embodiment, the invention relates to a pharmaceutical composition comprising vortioxetine pyroglutamate. A pharmaceutical formulation of the invention may be prepared by conventional methods in the art. Tablets may be prepared by mixing the active ingredient with ordinary carriers and/or diluents and subsequently compressing the mixture in a conventional tabletting machine. Examples of carriers or diluents comprise: anhydrous calcium hydrogen phosphate, PVP, PVP-VA co-polymers, microcrystalline cellulose, sodium starch glycolate, corn starch, mannitol, potato starch, talcum, magnesium stearate, gelatine, lactose, gums, and the like. Any other carriers or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

A pharmaceutical composition of the present invention may be administered by any suitable route, for example orally in the form of tablets, capsules, powders, syrups, etc., or parenterally in the form of solutions for injection. For preparing such compositions, methods well known in the art may be used, and pharmaceutically acceptable carriers, diluents, excipients or other additives normally used in the art may be used.

Conveniently, vortioxetine pyroglutamate is administered in a unit dosage form containing said compounds in an amount of about 1 to 50 mg (as free base). The total daily dose is usually in the range of about 1-20 mg, such as about 1 to 10 mg, about 5-10 mg, about 10-20 mg, or about 10-15 mg of the compound of the invention. Particular mention is made of daily doses of 5, 10, 15 or 20 mg.

The extreme solubility of vortioxetine pyroglutamate salts render these salts useful in the preparation of liquid formulations intended for e.g. infusion concentrates or oral drops. Oral drops is a highly concentrated liquid formulation intended for easy oral administration. When oral drops are administered, the patient or the care taker measures out a pre-determined volume of the oral drops which volume is mixed with a glass of drinkable liquid (water, juice etc), and the patient drinks the liquid. The administration form may be beneficial for e.g. elderly patients who have difficulties swallowing tablets or capsules.

The concentration of vortioxetine in oral drop formulations is determined by the number of drops (i.e. the volume) it is desired to collect and the amount of vortioxetine it is desired to administer. It is generally held that measuring out around 5-20 drops is an optimal compromise between safety/efficacy of the treatment on the one hand and convenience on the other. If the concentration of vortioxetine pyroglutamate is too high, i.e. if only a low number of drops is to be measured out, it may jeopardize safety or efficacy of the treatment. With a low number of drops, one or two drops more or less than desired will significantly increase the uncertainty in the dose provided. On the other hand, if the concentration of vortioxetine is too low, the number of drops to be measured out is high, which is inconvenient for the patient or the caretaker.

In addition to vortioxetine pyroglutamate, the oral drop formulation of the present invention may comprise pharmaceutically acceptable solvents, surface tension modifiers, viscosity modifiers, preservatives, antioxidants, colorants, taste maskers, flavours etc.

Examples of solvents include water and other solvents, which are miscible with water or solubilizing agents and suitable for oral purposes. Examples of suitable solvents are ethanol, propylene glycol, glycerol, polyethylene glycols, poloxamers, sorbitol and benzyl alcohol. The aqueous solubility of the active ingredient may further be enhanced by the addition to the solution of a pharmaceutically acceptable co-solvent, a cyclodextrin or a derivative thereof.

Surface tension modifiers may be included to adjust the drop number for the concentrated oral formulations. An example of a surface tension modifier is ethanol, which decreases the surface tension and increases the drop number.

Viscosity modifiers may be included to adjust the drop velocity for a concentrated oral formulation. The drop velocity for a formulation to be measured out in discrete drops from a container fitted with a drop aggregate should preferably not exceed 2 drops per second. Examples of viscosity modifiers include ethanol, hydroxyethylcellulose, carboxymethylcellulose sodium, methylcellulose, polyvinyl alcohol, polyvinylpyrrolidone, polyethylene glycol and glycerine.

Preservative agents may be added to prevent the growth of micro organisms such as bacteria, yeasts and fungi in liquid formulations, which are likely to be used repeatedly. Suitable preservatives should be physicochemical stable and effective in the desired pH range. Examples of preservative agents include ethanol, methylparaben, propylparaben and benzyl alcohol.

A drug substance is typically more sensitive to chemical degradation in dissolved than in solid form; hence it may be necessary to include an antioxidant in the liquid formulation. Examples of antioxidants include propyl gallate, ascorbyl palmitate, ascorbic acid, sodium sulphite, citric acid and EDTA.

Colouring agents may be used in some formulations to introduce a uniformity of appearance to the product. Some active ingredients may further be very sensitive to light and it may prove necessary to add colouring agents to the drop formulations to protect them from light and for the purpose of stabilization. Suitable colouring agents include for example tartrazine and sunset yellow.

Sweetening agents may mask unpleasant taste associated with some formulations or to achieve a desired taste. Examples of sweetening agents are glucose, sorbitol, glycerol, acesulfame potassium and neohesperidin dihydrochalcon. The taste may be optimized further by the addition of one or more flavouring substances. Suitable flavouring substances are fruit flavours such as cherry, raspberry, black currant, lemon or strawberry flavour or other flavours such as liquorice, anis, peppermint, caramel etc.

An oral drop formulation of the present invention may comprise
7.2% vortioxetine pyroglutamate (~5% free base)
0.08% methylparahydroxybenzoate
0.2% propylparahydroxybenzoate
Water q.s. ad 100%.

In one embodiment, the invention relates to a gelable pharmaceutical composition comprising vortioxetine pyroglutamate and a salt. In the present context, "gelable" indicates that a composition upon addition of an aqueous solution, such as water, forms a gel. This dry composition is easy to store and transport and therefore useful as a marketable product. In one embodiment, said pharmaceutical composition comprises vortioxetine pyroglutamate and a salt in a molar ratio of vortioxetine pyroglutamate:salt between 1:0.1 to 1:100, such as 1:0.5 to 1:50, such as 1:1 to 1:20. The gelable pharmaceutical composition of the present invention does not require gelling polymers in order to form a gel. In one embodiment, the gelable pharmaceutical composition of the present invention does not comprise gelling polymers. In the present context, "does not comprise" s intended to indicate that such polymers are not present in an amount that causes gelling of the formulation.

A "gelling polymer" in the present context is a polymer which upon mixing with an aqueous phase, such as water or water with $Ca^{++}$-ions gels or swells to form a gel. Examples of gelling polymers include starch, gellan, carboxymethylcellulose, pectin, alginate and gelatine. More examples of gelling polymers can be found, e.g. in Remington: The science and Practice of Pharmacy, 21$^{st}$ Edition, Lippincott, Williams & Wilkins, 2005.

In one embodiment, the invention relates to a gelable composition comprising vortioxetine pyroglutamate and a salt in a unit dose, wherein said unit dose comprises 1 mg-50 mg vortioxetine (as free base), such as 1, 5, 10, 15 or 20 mg vortioxetine (as free base).

Without being bound to a specific theory it is speculated that the gel-formation observed by the inventors is the result of the extreme solubility of vortioxetine pyroglutamate and the markedly lower solubility of other salts. Vortioxetine is initially brought into solution as the pyroglutamate salt. Eventually, vortioxetine will precipitate with the anion from the salt; however, a metastable gel is formed first which is sufficiently stable to render the gel useful for oral administration. Therefore, in the present context "salt" is intended to indicate a salt formed in a reaction between a pharmaceutically acceptable acid and a pharmaceutically acceptable base. Pharmaceutically acceptable acids include hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, glutamic acid, pyroglutamic acid, salicylic acid, salicylic acid and sulfonic acids, such as ethanesulfonic acid, toluenesulfonic acid and benzenesulfonic acid. Pharmaceutically acceptable bases include alkali metal bases, such as sodium hydroxide, lithium hydroxide, potassium hydroxide, alkaline earth bases, such as calcium hydroxide and magnesium hydroxide, and organic bases, such as ammonia, tri-methyl amine, tri ethyl amine. Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008. In particular, "salt" is intended to indicate a salt with an anion selected from chloride, bromide, fumerate, maleate, meso-tartrate, L-tartrate, D-tartrate, sulphate, phosphate and nitrate. In particular, "salt" is intended to indicate a salt with a cation selected from sodium, potassium, lithium, calcium, magnesium, ammonium, tri-methyl ammonium and tri-ethyl ammonium. In particular, "salt" is intended to indicate KBr, NaCl or NaBr. For the avoidance of doubt, "salt" does not include vortioxetine pyroglutamate.

In addition to vortioxetine pyroglutamate and a salt, a gelable pharmaceutical composition of the present invention may comprise other ingredients known in pharmaceutical science. Other ingredients may include taste modifiers, such as sweeteners and flavours. Examples of sweeteners include aspartame, acesulfame potassium, cyclamate, glycerrhizin, lactose, mannitol, cassahrin, sucrose and sucralose. Examples of flavours include ethyl vanillin, menthol, *glycyrrhiza*, fennel and lemon peel.

In one embodiment, the invention relates to a gel comprising vortioxetine pyroglutamate, a salt and water. A gel of the present invention does not require gelling polymers to form. In one embodiment, a gel of the present invention does not comprise gelling polymers. A gel of the present invention is particularly useful for oral administration because it is easily swallowed compared to other oral administration forms, in particular tablets and capsules. A gel of the present invention may comprise other ingredients known in pharmaceutical science, in particular taste modifiers, as discussed above. In the present context and in line with the USP definition of a gel, a gel is intended to indicate a semisolid system consisting of either small organic particles or large organic molecules interpenetrated by a liquid. A gel thus presents as a coherent, viscous, plastic or non-disintegrating phase. In practical terms, if vortioxetine pyroglutamate, a salt and an aqueous solution is mixed in a 4 ml vial as described example 1 and the vial, after shaking to allow a viscous phase to form, can be left upside down for 5 minutes within which said viscous phase essentially maintains its physical shape, and without said viscous phase disintegrates or leaves the vial, a gel is formed. In one embodiment, said gel comprises 1.5 mg-20 mg vortioxetine pyroglutamate per ml, such as 2 mg-15 mg per ml, such as 3 mg-10 mg per ml. In one embodiment, said gel comprises 0.1 M-1 M salt, such as 0.1 M-0.5 M salt, such as 0.1 M-0.3 M salt. In one embodiment, said gel comprises 0.5-20 mg vortioxetine pyroglutamate pr ml and 0.1 M-1 M salt, such as 0.1 M-0.5 M salt, such as 0.1 M-0.3 M salt. The amounts of vortioxetine pyroglutamate are indicated as free base. It is the experience of the inventors that the volume of the aqueous phase and the final gel are roughly similar when the gel comprises a therapeutically relevant dose in a therapeutically relevant volume.

The gel of the present invention is formed by mixing vortioxetine pyroglutamate, a salt and an aqueous solution, typically water. Gel formation is not sensitive to the mixing order, and vortioxetine pyroglutamate and/or the salt may be brought into solution prior to mixing with the other ingredients. In one embodiment, the invention relates to a gel formed by mixing vortioxetine pyroglutamate, a salt and water. In one embodiment, vortioxetine pyroglutamate and a salt is mixed in an essentially dry state and an aqueous solution, such as water is added to form the gel.

In one embodiment, the invention relates to a method of forming a gel, the method comprising mixing vortioxetine pyroglutamate, a salt and an aqueous solution, such as water.

The international patent applications published as WO 2011/023194 and WO 2011/136376 disclose enteric coated formulations comprising vortioxetine. In particular WO 2011/023194 discloses an experiment in which a radio guided capsule (Enterion™) was administered to subjects as part of a 5-way crossover study (See example 1 of '194). In said study the bioavailability and gastro intestinal (GI) tract adverse events were compared between 20 mg vortioxetine HBr instant release (IR), 9 mg vortioxetine HBr IV, and 20 mg HBr solution released to the small intestines (either the proximal bowel or the distal bowel). The fifth arm was without active compound.

The results showed unexpectedly that plasma concentration-time profiles are almost identical for 20 mg vortioxetine HBr IR formulation and 20 mg vortioxetine HBr solution released to the proximal or distal bowel. Put differently, the three formulations were bioequivalent. Moreover, the results showed a markedly lower level of GI tract adverse events, in particular a lower level of nausea and diarrhoea for the two formulations released to the intestines compared to the IR formulation. In combination the results disclosed in WO 2011/023194 show that vortioxetine released to the intestines (e.g. in an enteric formulation) is associated with a superior GI tract adverse event profile compared to vortioxetine administered in an IR formulation while delivering the same plasma concentration, hence achieving the same therapeutic effect.

However, as shown in Example 17 vortioxetine HBr has inadequate bioavailability in an enteric coated tablet and therefore fails to be useful as such. Example 17 is a 4-arm human study in healthy volunteers comparing the plasma concentration-time profiles for 20 mg vortioxetine HBr administered as IR and in enteric coated formulations with releases at pH 5.5, 6.0 and 7.0. pH in the stomach is very acidic and around 1-1.5. pH increases sharply from the stomach into the small intestines and increases from around 5.5 to 7.5 from the proximal to the distal parts [Adv Drug Deliv, 25, 3-14, 1997]. The release pH's investigated for the enteric coated formulations thus span release over the entire length of the small intestines. As shown in FIG. 13, the enteric coated formulations have a markedly decreased bioavailability with $AUC_{0-72\,h}$ (Area Under the Curve) around 50% for the two enteric coated formulations with release pH at 5.5 and 6.0 and around 10% for the enteric coated formulation with release pH of 7.0 (relative to $AUC_{0-72\,h}$ for the IR tablet).

The enteric coated vortioxetine HBr tablet is therefore not bioequivalent to a vortioxetine HBr IR formulation and, as a consequence hereof, will not provide the same therapeutic effect. It cannot be ruled out that increasing the amount of vortioxetine HBr in an enteric coated tablet could increase AUC; however for several reasons this may not be possible or desirably. First, increasing the dose in an enteric coated tablet may result in a different shape of the plasma concentration-time profile for which reason bioequivalence cannot be obtained. Second, each patient has different uptake of any given drug, and exposure of all patients to high doses increases the risk of unexpected high and unwanted drug absorption and the safety concerns associated therewith.

The slopes of the rising parts of the plasma concentration-time profiles depicted in FIG. 13 indicate that the dissolution rate for vortioxetine HBr in the intestines is markedly lower than that in the stomach. It is suggested that an inadequate dissolution rate of vortioxetine HBr at intestine relevant pH causes the compound not to be available for absorption from the intestines into the plasma and therefore not to be suitable for administration in an enteric coated formulation.

The data reported in Example 18 shows the dissolution rate for vortioxetine HBr and vortioxetine pyroglutamate. The results show that the pyroglutamic acid salt of vortioxetine has a markedly higher dissolution rate compared to the HBr salt.

The experiment reported in Example 19 was conducted to test the hypothesis that a high dissolution rate for a vortioxetine salt is indicative for bioequivalence compared to a vortioxetine HBr IR tablet when said salt is provided in an enteric coated formulation. The study is a 4-arm crossover study in dogs comparing the plasma concentration-time profiles for vortioxetine HBr administered in an IR formulation, vortioxetine HBr administered in an EC formulation; vortioxetine HBr administered as an oral solution, and vortioxetine pyroglutamate administered as an EC formulation. As seen from the data presented in FIG. 14, the plasma concentration-time profiles for vortioxetine HBr in IR formulation and vortioxetine pyroglutamate in EC formulation are similar apart from a time-shift due to the delayed release. In comparison hereto, vortioxetine HBr in EC formulation has a very different profile with a much lower AUC. The initial slopes on the plasma concentration-time slopes in FIG. 14 also confirm that the dissolution rate for vortioxetine HBr in IR formulation and vortioxetine pyroglutamate in EC formulation is almost identical and much larger than that for vortioxetine HBr in EC formulation. The similarity between the data obtained in Examples 17 and 19 serves to validate the results obtained in the dog study.

The data obtained in Example 19 shows that vortioxetine pyroglutamate in an EC formulation provides a plasma concentration-time profile which is similar to that from vortioxetine HBr in an IR tablet. Based on this similarity it is concluded that a similar therapeutic effect is obtained from two such formulations. In addition, the data disclosed in WO 2011/023194 shows that if vortioxetine is released in the intestines rather than in the stomach it is associated with a marked decrease in gastrointestinal adverse events. In the result, treatment of patients with vortioxetine pyroglutamate salt in solid enteric coated formulation is expected to provide the same therapeutic effect and with a lower level of gastrointestinal adverse events compared to treatment with vortioxetine HBr in a solid IR formulation. This is in contrast to treatment with vortioxetine HBr in enteric coated tablets which is associated with a much lower absorption of the active ingredient, and a consequent inferior therapeutic effect.

Vortioxetine HBr in an IR formulation is now approved in many major markets. A new formulation of vortioxetine which is bioequivalent to the existing, approved IR formulation can in many countries rely on the regulatory safety and efficacy data on which the vortioxetine HBr IR formulation was approved for its own approval. Hence, bringing an enteric coated formulation of vortioxetine pyroglutamate to the market can be done without the need for lengthy and expensive clinical studies.

In one embodiment, the invention provides an enteric coated formulation comprising vortioxetine pyroglutamate. In particular said enteric formulation is solid and for oral administration. In one embodiment, said vortioxetine pyroglutamate is either of vortioxetine (DL)-pyroglutamate α-form, vortioxetine (L)-glutamate, vortioxetine (D)-pyroglutamate, vortioxetine (DL)-pyroglutamate mono hydrate, or mixtures thereof.

The total daily dose is typically between 1 and 50 mg vortioxetine (free base), such as 1-10 mg, such as 5, 10, 15 or 20 mg.

In the present context, "enteric coated" is intended to indicate a pH sensitive coating which essentially does not allow vortioxetine to be released or dissolved in the stomach but essentially only in the intestines. A useful two-stage in vitro dissolution test is as follows. Equipment: Standard USP rotating paddle apparatus; paddle speed 75 rpm; 37° C. First stage: A unit dose is exposed to 600 ml 0.1 M HCl for 2 hours. Second stage: The unit dose is transferred to 900 ml TRIS buffer (0.6 M) with 0.3 w/w-% cetyl trimethylammonium bromide at pH at or above 5.5 for 2 hours. Samples are withdrawn at suitable time points and analysed for vortioxetine to determine the amount of vortioxetine released. The pH in the second stage may be adjusted to more specifically determine where in the intestines the drug is released. For example, pH in the second stage may be 5.5, 6.0, 6.5, or 7.0. A unit dose typically comprises 1-50 mg vortioxetine. In one embodiment, if a coated formulation releases less than 10%, such as less than 5% of the unit dose in first stage, and the balance in second stage, said coated formulation is said to be enteric coated. The use of TRIS buffer is not critical, and other buffers may be used.

Enteric coating include pH sensitive polymers, such as polyacrylamides, phthalate derivatives such as acid phthalates of carbohydrates, amylose acetate phthalate, cellulose acetate phthalate, other cellulose ester phthalates, cellulose ether phthalates, hydroxypropyl cellulose phthalate, hydroxypropylethyl cellulose phthalate, hydroxypropylmethyl cellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Anionic acrylic copolymers of methacrylic acid and methylmethacrylate or ethyl acrylate are particularly useful pH dependent coating materials. Enteric coatings of this type are available from Degussa under the tradename Eudragit. Particularly useful are the products Eudragit L 30 D-55, which comprises poly(methacrylic acid-co-ethyl acrylate) 1:1 with a molecular weight around 320,000 g/mol which provides dissolution at pH above 5.5; Eudragit L100 which comprises poly(methacylic acid-co-methyl methacrylate) 1:1 with a molecular weight around 125,000 g/mol which provides dissolution at pH above 6.0; and Eudragit FS 30 D which comprises poly(methyl acrylate-co-methyl methacrylate-co-methacrylic acid) 7:3:1 with a molecular weight around 280.00 g/mol which provides dissolution above pH 7.0. Thus, by applying either of the Eudragit polymers in pure form or as mixtures thereof, it is possible to control where in the intestine release takes place.

In one embodiment, a unit dose of the enteric coated formulation of the present invention is comprised in a single or a few tablets. Alternatively, a unit dose of the enteric coated formulation of the present invention is comprised in a multiple (such as e.g. 20-60) of smaller tablets. Said tablet(s) may be presented in a capsule wherein said capsule rather than the individual tablet(s) is/are enteric coated.

In one embodiment, the enteric coated formulation of the present invention is a multiparticulate formulation wherein a unit dose of the enteric coated formulation is comprised in a multiple of tablets each tablet being enteric coated. This is often referred to as enteric coated mini-tablets. This embodiment has the added advantage of being less sensitive to damages to the coating which could result in dose dumping.

The enteric coated formulation of the present invention may be prepared by applying vortioxetine pyroglutamate on an inert core by drug-layering techniques, such as powder-coating, or by spraying a solution of vortioxetine pyroglutamate and a suitable binder onto a core, e.g. in a fluidized bed coater or a rotary mixer. The resulting cores are subsequently coated with a suitable enteric coating. These particles may be compressed into a tablet or presented in a capsule, as a powder or in a sachet.

Enteric coated tablets may be prepared in a number of ways available to the skilled person. Tablets may be prepared by mixing vortioxetine pyroglutamate with ordinary adjuvants and/or diluents and subsequently compressing the mixture in a conventional tabletting machine. Examples of adjuvants or diluents include PVP, PVP-VA co-polymers, microcrystalline cellulose, sodium starch glycolate, corn starch, mannitol, potato starch, talcum, magnesium stearate, gelatine, lactose, gums, croscarmellose sodium and the like. Any other adjuvants or additives usually used for purposes such as colourings, flavourings, preservatives etc. may be used provided that they are compatible with the other ingredients. The tablets obtained are subsequently coated with a suitable enteric coating, e.g. by spraying a solution comprising the coating material onto the tablets.

In one embodiment, the invention provides an enteric formulation comprising vortioxetine pyroglutamate in a tablet, which tablet is coated with poly(methacrylic acid-co-ethyl acrylate) 1:1 with a molecular weight around 320,000 g/mol, or poly(methacylic acid-co-methyl methacrylate) 1:1 with a molecular weight around 125,000 g/mol, or poly (methyl acrylate-co-methyl methacrylate-co-methacrylic acid) 7:3:1 with a molecular weight around 280,000 g/mol.

In the present context "molecular weight" is intended to indicate "Weight average molar mass".

In one embodiment, the invention provides an enteric formulation comprising vortioxetine pyroglutamate, mannitol, microcrystalline cellulose, sodium starch glycolate, hydroxypropyl cellulose and magnesium stearate in a tablet, which tablet is coated with poly(methacrylic acid-co-ethyl acrylate) 1:1 with a molecular weight around 320,000 g/mol, or poly(methacylic acid-co-methyl methacrylate) 1:1 with a molecular weight around 125,000 g/mol, or poly(methyl acrylate-co-methyl methacrylate-co-methacrylic acid) 7:3:1 with a molecular weight around 280,000 g/mol.

In one embodiment, the invention provides an enteric coated formulation comprising vortioxetine pyroglutamate, microcrystalline cellulose, croscarmellose sodium and magnesium stearate in a tablet, which tablet is coated with poly(methacrylic acid-co-ethyl acrylate) 1:1 with a molecular weight around 320,000 g/mol, or poly(methacylic acid-co-methyl methacrylate) 1:1 with a molecular weight around 125,000 g/mol, or poly(methyl acrylate-co-methyl methacrylate-co-methacrylic acid) 7:3:1 with a molecular weight around 280,000 g/mol. In particular, said formulation comprises 10% vortioxetine pyroglutamate, 86 w/w-% microcrystalline cellulose, 3 w/w-% croscarmellose sodium and 1 w/w-% magnesium stearate before coating. In particular, each tablet comprises 1 mg vortioxetine (as free base).

Vortioxetine is approved by several health authorities for the treatment of major depression or major depressive episode. As disclosed in e.g. WO 03/029232 and WO 2007/144005 the pharmacological profile of vortioxetine is expected to also make the compound useful in the treatment of general anxiety disorder, obsessive compulsive disorder (OCD), panic disorder; post-traumatic stress disorder; cognitive impairment; mild cognitive impairment (MCI); cognitive impairment associated with Alzheimer's disease, depression or schizophrenia (CIAS); and attention deficit hyperactivity disorder (ADHD).

Cognitive deficits, cognitive impairment or cognitive dysfunction include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive deficits may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts. The terms "cognitive deficits", "cognitive impairment" and "cognitive dysfunction" are intended to indicate the same and are used interchangeably.

In one embodiment, the invention relates to the use of vortioxetine pyroglutamate in the manufacture of a medicament for the treatment of a disease selected from major depressive disorder; major depressive episode: general anxiety disorder; obsessive compulsive disorder (OCD), panic disorder; post traumatic stress disorder; cognitive impairment; mild cognitive impairment (MCI); cognitive impairment associated with Alzheimer's disease, depression or schizophrenia (CIAS); and attention deficit hyperactivity disorder (ADHD).

In one embodiment, the invention relates to the use of vortioxetine pyroglutamate and a salt in the manufacture of a medicament for the treatment of a disease selected from major depressive disorder; major depressive episode; general anxiety disorder, obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD).

In one embodiment, the invention relates to vortioxetine pyroglutamate for use in a method for the treatment of a disease selected from major depressive disorder; major depressive episode; general anxiety disorder, obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD).

In one embodiment, the invention relates to vortioxetine pyroglutamate and a salt for use in a method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD).

In one embodiment, the invention relates to a method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount vortioxetine pyroglutamate to a patient in need thereof.

In one embodiment, the invention relates to a method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount of a gel comprising vortioxetine pyroglutamate, a salt and water to a patient in need thereof.

In one embodiment, the invention relates to a method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount of a gel prepared by mixing a therapeutically effective amount of vortioxetine pyroglutamate, a salt and an aqueous solution, such as water, to a patient in need thereof.

In one embodiment, the patient treated according to the method of the present invention has been diagnosed with the indication for which said patient receives treatment.

In the present context, "treatment" or "treating" is intended to indicate the management and care of a patient for the purpose of alleviating, arresting, partly arresting or delaying progress of the clinical manifestation of the disease, or curing the disease. The patient to be treated is preferably a mammal, in particular a human being.

In the present context, "therapeutically effective amount" is intended to indicate an amount of a compound which in a treatment comprising the administration of said compound to a patient achieves a treatment effect.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector.

Differential Scanning Calorimetry thermograms were obtained on equipment from TA Instruments (DSC-Q2000) calibrated at 5° C./minute to give the melting point as onset value. Approximately 2 mg of the sample was heated at 5° C./minute in a closed pan with a pinhole in the lid and under nitrogen flow.

Thermo gravimetric analysis thermograms used for measurement of solvent/water content of dried samples was performed using a TA-Insstruments TGA-Q500. 1-10 mg sample was heated at 10° C./minute in a open pan under nitrogen flow.

Dynamic Vapour Sorption spectra were obtained on equipment from SMS Systems (DVS Advantage). The change in mass (relative to the dry state) of a sample (10-20 mg) was determined as a function of the relative humidity (P/P$_0$) at 25° C.

The gelling experiments were carried out in a 4 ml cylindrical vial with an inner diameter of approximately 1 cm.

Example 1—Vortioxetine (DL)-Pyroglutamate Gel

To 5.5 mg vortioxetine (DL) pyroglutamate MH in a 4 mL vial was added a solution of potassium bromide in water (0.17 M, 1.0 mL) and the resulting mixture was shaken for 5 seconds. After standing for less than 1 minute a clear gel was formed. The vial was left standing upside down for more than 1 hour during which the gel properties of the gel were maintained and the gel remained in the top (bottom) of the vial.

Example 2—Vortioxetine (DL)-Pyroglutamate Gel

To 10.2 mg vortioxetine (DL)- pyroglutamate α-form in a 4 mL vial was added a solution of potassium bromide in water (0.23 M, 1.0 mL) and the resulting mixture was shaken for 5 seconds. After standing for less than 1 minute a clear gel was formed. The vial was left standing upside down for more than 1 hour during which the gel properties of the gel were maintained and the gel remained in the top (bottom) of the vial.

Example 3—Vortioxetine (DL)-Pyroglutamate Gel

To 6.2 mg vortioxetine (DL)-pyroglutamate MH in a 4 mL vial was added water (0.15 mL) and a solution of sodium bromide in water (0.307 M, 0.85 mL, total 0.26 M) and the resulting mixture was shaken for 5 seconds. After standing for less than 1 minute a clear gel was formed. The vial was left standing upside down for more than 30 minutes during which the gel properties of the gel were maintained and the gel remained in the top (bottom) of the vial.

Example 4—Vortioxetine (DL)-Pyroglutamate Gel

To 10.7 mg vortioxetine (DL)-pyroglutamate MH in a 4 mL vial was added water (0.35 mL) and a solution of sodium bromide in water (0.307 M, 0.65 mL, total 0.20 M) and the resulting mixture was shaken for 5 seconds. After standing for less than 1 minute a clear gel was formed. The vial was left to stand upside down for more than 1 hour during which the gel properties of the gel were maintained and the gel remained in the top (bottom) of the vial.

Example 5—Vortioxetine (DL)-Pyroglutamate Gel

To 0.80 g vortioxetine (DL)-pyroglutamate MH in a 250 mL round-bottomed flask was added a solution of sodium chloride in water (0.20 M, 100 mL) and the resulting mixture was shaken for 5 seconds. After standing for 2 minute a clear gel was formed. The flask was left to stand upside down for more than 30 minutes during which the gel properties were maintained and the gel remained in the top (bottom) of the flask.

Example 6—Vortioxetine (DL)-Pyroglutamate Gel

To 8.0 mg vortioxetine (DL)-pyroglutamat MH in a 4 mL vial was added water (0.15 mL) and a solution of sodium chloride in water (0.31 M, 0.85 mL, total 0.26 M) and the resulting mixture was shaken for 5 seconds. After standing for 6 minute a clear gel was formed. The vial was left to stand upside down for more than 1 hour during which the gel properties of the gel were maintained and the gel remained in the top (bottom) of the vial.

Example 7—Vortioxetine (DL)-Pyroglutamate Gel

To 11.2 mg vortioxetine (DL)-pyroglutamate MH in a 4 mL vial was added water (0.20 mL) and a solution of sodium chloride in water (0.31 M, 0.80 mL, total 0.25 M) and the resulting mixture was shaken for 5 seconds. After standing for 5 minute a clear gel was formed. The vial was left to stand upside down for more than 30 minutes during which the gel properties of the gel were maintained and the gel remained in the top (bottom) of the vial.

Example 8—Vortioxetine (L)-Pyroglutamate Gel

To 7.6 mg vortioxetine (L)-pyroglutamate in a 4 mL vial was added a solution of sodium bromide in water (0.18 M, 1.0 mL) and the resulting mixture was shaken for 5 seconds. After standing for less than 1 minute a clear gel was formed. The vial was left to stand upside down for more than 30 minutes during which the gel properties of the gel were maintained and the gel remained in the top (bottom) of the vial.

Example 9—Vortioxetine (DL)-Pyroglutamate Gel 14 mg vortioxetine (DL)-pyroglutamate MH in a 4 mL vial was added sodium chloride (26 mg) and water (2.0 mL) and the resulting mixture was shaken for 5 seconds. After standing for less than 1 minute gel was formed. The vial was left to stand upside down for more than 10 minutes during which the gel properties of the gel were maintained and the gel remained in the top (bottom) of the vial.

Example 10—Preparation of Vortioxetine (L)-Pyroglutamate

Vortioxetine (2.98 g) was dissolved in 2-propanol (15 mL) at 60° C. To this stirred reaction mixture was drop-wise added a warm solution (60° C.) of L-pyroglutamic acid (1.29 g) in 2-propanol (15 mL). The reaction was cooled to room temperature over a 2 hour period and then cooled to 0-5° C. for 1.5 h prior to filtration. Vortioxetine (L)-pyroglutamate was isolated by filtration. The filter cake was washed with 2-propanol (2×5 mL) and dried under vacuum overnight to yield 4.09 g (96% yield).

$^1$H NMR (DMSO-d$_6$): 7.65 (s, 1H), 7.33 (d, 1H), 7.24 (s, 1H), 7.10 (m, 3H), 6.93 (dd, 1H), 6.40 (d, 1H), 3.87 (dd, 1H), 3.10 (bs, 8H), 2.32 (s, 3H), 2.24 (s, 3H), 2.23 (mp, 1H), 2.08 (mp, 2H), 1.95 (mp, 1H).

Example 11—Characterization of Vortioxetine (L)-Pyroglutamate

Elemental analysis of the product obtained in Example 10 gave the following results: 63.5% C, 6.95% H, 9.44% N, Karl Fisher (KF): 1.6% water (Theory corrected for 1.6% water: 63.58% C, 6.91% H, 9.67% N).

XRPD spectrum of the product obtained in Example 10 is shown in FIG. 1. The spectrum shows that the product is essentially in a crystalline form. Vortioxetine (L)-pyroglutamate has characteristic XRPD reflections at 10.72, 12.14, 16.22 and 18.59 (°2θ); such as 10.72, 12.14, 16.05, 16.22, 17.53, 17.70, 18.45 and 18.59 (°2θ), such as 7.02, 10.72, 12.14, 14.45, 14.61, 15.56, 16.05, 16.22, 17.53, 17.70, 18.45 and 18.59 (°2θ). All values are ±0.1°2θ.

TGA thermogram of the product obtained in Example 10 is shown in FIG. 2. An initial loss of water is followed by a small weight loss which is probably from solvent trapped in the crystals released during melting.

DSC thermogram of the product obtained in Example 10 is shown in FIG. 3. After an initial loss of water, there is a sharp melting peak at 138.9° C. (onset value).

DVS spectrum of the product obtained in Example 10 is shown in FIG. 4. The sample contained 4% water when the measurement was initiated. Further 2.7% is gradually absorbed as the humidity increases up to 95% Relative Humidity. All water is gradually released as the humidity is lowered to 0% RH. It may be noted that the sample appears to have absorbed water between the KF water content determination and the DVS measurement.

To 500 mg vortioxetine (L)-pyroglutamate was added 900 µl water at 21° C. The viscous solution containing weak precipitation was centrifuged, filtered and the concentration of the supernatant was determined by HPLC after dilution.
HPLC Method:
Column: . . . X-Bridge C18, 150*4.6 mm ID, 3.5 µm or equivalent
Mobile Phase: . . . 25 mM phosphatebuffer pH6.0/MeOH (35/65)
Column Temperature: . . . 45° C.
Detector: . . . UV at 225 nm
Flow: . . . 1 ml/min
Injection volume: . . . 10 µl
Time of Analysis: . . . 5 minutes
The results showed that vortioxetine (L)-pyroglutamate has a solubility of 225 mg/ml.

Example 12—Preparation of Vortioxetine (DL)-Pyroglutamate MH

Vortioxetine HBr salt (750 g), (DL)-pyroglutamic acid (250 g) and methyl tetrahydrofuran (10 L) were mixed in a reactor. To this mixture was added sodium hydroxide solution (1 M, 3.4 L) and the mixture was then heat to approximately 40° C. Once a clear solution was formed, the stirring was stopped and the reaction was allowed to stand to allow the phases to separate. The organic phase was retained and the water phase was discarded. The organic phase was washed with water (3 L) and followed by sodium hydroxide solution (1 M, 2 L) and stirred for 30 minutes after which the stirring was stopped and the reaction was allowed to stand to allow the phases to separate. The organic phase was retained and the water phase was discarded. (DL)-pyrogultamic acid (0.250 kg) was added to the organic phase and then reduced in volume by distillation (approx 5.3 L removed by distillation). The mixture was allowed to cool and the product isolated by filtration. The filter cake was washed with cold methyl tetrahydrofuran (2.5 L) and dried under reduce pressure at 40° C. to give the desired vortioxetine (DL)-pyrogultamate MH salt (705 g). The initial addition of (DL)-pyroglutamic acid was an error. This error has no impact on the outcome of the synthesis.

Example 13—Characterization of Vortioxetine (DL)-Pyroglutamate MH

Elemental analysis of the product obtained in Example 12 gave the following results: 61.94% C, 6.99% H, 9.40% N (theory for a monohydrate: 62.00% C, 7.01% H, 9.43% N)

XRPD spectrum of the product obtained in example 12 is shown in FIG. 5. The spectrum shows that the product is essentially in a crystalline form. Vortioxetine (DL)-pyroglutamate MH has characteristic XRPD reflections at 6.16, 9.25, 17.68 and 18.12 (°2θ), such as at 6.16, 9.25, 14.61, 15.02, 15.88, 16.33, 17.68 and 18.12 (°2θ), such as at 6.16, 9.25, 9.38, 12.10, 14.03, 14.61, 15.02, 15.88, 16.33, 16.91, 17.68 and 18.12 (°2θ). All values are ±0.1 °2θ.

DSC thermogram of the product obtained in Example 12 is shown in FIG. 6. After desolvation (1$^{st}$ broad peak at ~95° C.) the alpha form is formed, which then melts.

The two-step weight loss corresponding to desolvation can also be identified in the TGA thermogram of the product obtained in example 12 shown in FIG. 7.

DVS spectrum of the product obtained in example 12 is shown in FIG. 8. Vortioxetine (DL)-pyroglutamate MH is not hygroscopic up to 80% relative humidity at 25° C. At 90% relative humidity some water is absorbed and at 95% relative humidity it is hygroscopic. Equilibrium is not reached thus more than 10% is absorbed and a sample stored at 95% relative humidity for prolonged period of time becomes liquid.

200 mg vortioxetine (DL)-pyroglutamate MH was dissolved in 200 µl water at room temperature. Due to the changes in volume induced, the concentration was calculated to 278 mg/ml. From this a solubility of at least 278 mg/ml is determined.

Example 14—Preparation of Vortioxetine (DL)-Pyroglutamate α-Form

Vortioxetine HBr salt (750 g) and methyl tetrahydrofuran (10 L) were mixed in a reactor. To this mixture was added sodium hydroxide solution (1 M, 3.4 L) and the mixture was then heated to approximately 40° C. Once a clear solution was formed the stirring was stopped and the reaction was allowed to stand to allow the phases to separate. The organic phase was retained and the water phase was discarded. Organic phase was washed with water (3 L) and (DL)-pyrogultamic acid (0.250 kg) was added to the organic phase and then reduced in volume by distillation (approximately 7 L removed by distillation). Additional methyl tetrahydrofuran was added (2 L) and distilled a little further until the reaction mixture was approximately 77° C. The mixture was then cooled down to approximately 10° C. and the product isolated by filtration. The filter cake was washed with cold methyl tetrahydrofuran (2 L) and dried under reduced pressure to give the desired vortioxetine (DL)-pyrogultamate α-form salt (807 g).

Example 15—Characterisation of Vortioxetine (DL)-Pyroglutamate α-Form

Elemental analysis of the product obtained in Example 14 gave the following results: 64.52% C, 6.83% H, 9.73% N (Theory: 64.61% C, 6.84% H, 9.83% N).

XRPD spectrum of the product obtained in Example 14 I shown in FIG. 9. The spectrum shows that vortioxetine (DL)pyroglutamate α-form is essentially in a crystalline form. Vortioxetine (DL)pyroglutamate α-form has characteristic XRPD reflections at 14.27, 15.75, 17.06 and 18.59 (°2θ), such as at 7.42, 10.78, 13.58, 14.27, 14.60, 15.75, 17.06 and 18.59(°2θ), such as at 7.42, 10.78, 13.58, 13.99, 14.27, 14.60, 15.75, 15.90, 16.89, 17.06, 17.87 and 18.59 (°2θ). All values are ±0.1°2θ.

DSC thermogram of the product obtained in Example 14 is shown in FIG. 10. Vortioxetine (DL)pyroglutamate α-form has a melting point 178.2° C. (onset value).

TGA thermogram of the product obtained in Example 14 is shown in FIG. 11. As evidenced by the data, vortioxetine (DL)pyroglutamate α-form has no weight loss before the melting point.

DVS spectrum of the product obtained in example 14 is shown in FIG. 12. The spectrum shows that show that vortioxetine (DL)pyroglutamate α-form is not hygroscopic. Less than 0.3% was absorbed up to 95% relative humidity.

200 mg vortioxetine (DL)-pyroglutamate α-form was dissolved in 200 µl water at room temperature. Due to the changes in volume induced, the concentration was calculated to 278 mg/ml. From this a solubility of at least 278 mg/ml is determined.

Example 16—Preparation of Vortioxetine (DL)-Pyroglutamate α-Form

Vortioxetine HBr salt (750 g), methyl tetrahydrofuran (10.5 L) and water (3 L) were stirred in a reactor. To this mixture was added sodium hydroxide solution (27.7%, 3.8 L) and the mixture was heat to approximately 70° C. Once a clear solution was formed the stirring was stopped and the reaction was allowed to stand to allow the phases to separate. The organic phase was retained and the water phase was discarded. DL-pyrogultamic acid (0.263 kg) was added to the organic phase which was then reduced in volume by distillation (approx 8 L removed by distillation). The mixture was then cooled down to approximately 10° C. and the product isolated by filtration. The filter cake was washed with cold methyl tetrahydrofuran (2 L) and dried under reduce pressure to give the desired vortioxetine (DL)-pyrogultamate α-form salt (803 g). The crystalline form was confirmed by XRPD.

Example 17 Clinical Study with Vortioxetine HBr in Enteric Coated Formulation Three different enteric coated formulations were prepared with identical cores a shown below:

| | |
|---|---|
| Dose (mg) | 1 |
| Tablet mass (mg) | 15 |

| | % w/w |
|---|---|
| Vortioxetine HBr | 8.47 |
| Microcrystalline cellulose | 15.00 |
| Mannitol | 69.53 |
| Hydroxypropylcellulose | 3.0 |
| Sodium starch glycolate (Type A) | 3.0 |
| Magnesium stearate | 1.0 |
| Sum | 100 |

Vortioxetine HBr (particle size distribution $X_{10}$ 1.9 µm; $X_{50}$ 9.3 µm; $X_{90}$ 49 µm; $X_{99}$ 150 µm, all volume mean diameter) was mixed with mannitol, microcrystalline cellulose and hydroxypropylcellulose in a fluid bed and granulation water was added, and the mixture was allowed to granulate upon which the granules were dried and sieved. The granules were mixed with microcrystalline cellulose and sodium starch glycolate (type A) in a blender together with magnesium stearate. The resulting granules were pressed into tablet cores using 3 mm punches.

The core tablets were subsequently coated with a subcoating of Opadry Pink (3.5% w/w) and three different enteric coatings to achieve release at pH above 5.5, pH above 6.0 and pH above 7.0. The coating suspensions are indicated below. Eudragite L 30 D-55, Eudragite L100 and Eudragite FS 30 D were applied corresponding to 15.3 mg/cm², 18 mg/cm² and 11 mg/cm², respectively.

The sub-coat is applied to make the mini-tablet more spherical to achieve a more homogeneous coating with the enteric polymer. Opadry Pink is a coloured coating comprising hypromellose type 2910, titanium dioxide, polyethylene glycol 400 and iron oxide red. The compositions of Eudragite L 30 D-55, Eudragite L100 and Eudragite FS 30

D are discussed above. PlasAcryl T20 is a commercially available plasticizer comprising glycerol monostearate, triethyl cistrate and polysorbate 80.

| % w/w | Opadry | L 30 D-55 Release at pH above 5.5 | L 100 Release at pH above 6.0 | FS 30 D Release at pH above 7.0 |
|---|---|---|---|---|
| Opadry | 15 | | | |
| Eudragit L 30 D-55 | | 57.9 | | |
| Eudragit L100 | | | 9.95 | |
| Eudragit FS 30 D | | | | 60.6 |
| Triethyl citrate | | 0.9 | 4.98 | |
| Talc | | | 4.98 | |
| Glycerol monostearate | | | | 0.72 |
| 1N NH$_3$ | | | 5.6 | |
| PlasAcryl T20 | | 8.7 | | 9.1 |
| Water | 85 | 32.5 | 74.49 | 29.58 |
| Total (%) | 100 | 100 | 100 | 100 |

Capsules containing mini-tablets as prepared above (20 mg vortioxetine free base) were tested together with 20 mg IR tablet (commercial, encapsulated) in a single-centre, randomised, double-blind, 4-way crossover, single-dose study in healthy women. Each dosing was separated by at least 21 days wash-out period. Following dosing blood samples were drawn at pre-determined points up to 72 hours for analysis of vortioxetine plasma levels.

The commercial 20 mg tablet comprises mannitol, microcrystalline cellulose, hydroxypropylcellulose, sodium starch glycolate, magnesium stearate and a film coating which consists of hypromellose, titanium dioxide, polyethylene glycol 400 and colorant.

The table below gives the mean pharmacokinetic data for each of the four arms, and the plasma concentration-time profiles are shown in FIG. 17.

| | 20 mg IR N = 37 | 20 mg enteric coated (pH 5.5) N = 36 | 20 mg enteric coated (pH 6.0) N = 38 | 20 mg enteric coated (pH 7.0) N = 35 |
|---|---|---|---|---|
| AUC$_{0-72\,h}$ (ng h/ml) | 366 | 201 | 214 | 46.8 |
| C$_{max}$ (ng/ml) | 9.84 | 4.37 | 4.77 | 0.797 |

Relevant statistical data are shown below:

| Parameter | Comparison (Test v Reference) | Ratio and 90% CI of the Ratio (Test:Reference) |
|---|---|---|
| AUC$_{0-72\,h}$ (ng h/ml) | 20 mg EC pH 5.5 v 20 mg IR | 0.555 (0.505, 0.610) |
| | 20 mg EC pH 6.0 v 20 mg IR | 0.599 (0.556, 0.646) |
| | 20 mg EC pH 7.0 v 20 mg IR | 0.0991 (0.0802, 0.122) |
| C$_{max}$ (ng/ml) | 20 mg EC pH 5.5 v 20 mg IR | 0.404 (0.330, 0.494) |
| | 20 mg EC pH 6.0 v 20 mg IR | 0.484 (0.444, 0.528) |
| | 20 mg EC pH 7.0 v 20 mg IR | 0.0497 (0.0372, 0.0664) |

CI: Confidence interval.
Bioequivalence typically requires the ratio to be between 0.8 and 1.15.

Example 18 Intrinsic Dissolution Rate for Vortioxetine Salts

The intrinsic dissolution rate (IDR) is expressed as mg vortioxetine dissolved per cm$^2$ surface per min. The intrinsic dissolution rate is measured using the "spinning-disc method" (μDISS Profiler Instrument from Pion Instruments).

In order to define the surface from which the test compound dissolves, miniaturized disks of compacted pure test compound are made (10 mg). The disk holding the test compound is inserted into a Teflon cup containing an imbedded magnet. The cup is inserted into a vial containing 20 ml dissolution medium (37° C./200 RPM). The dissolved test compound is measured by a fibre optic detection system (200-400 nm). The concentration is determined by comparison with a standard solution and the calculated amount of test compound released (as free base) per surface area is plotted versus time. The slope gives the intrinsic dissolution rate. The measurements are performed in duplicate. The dissolution medium was 50 mM Tris at pH 6.8. Vortioxetine HBr β-form is defined in WO 2007/144005 (see e.g. example 4c and 4d).

| Salt | IDR (mean of 2 determinations (mg/cm2/min) |
|---|---|
| HBr (β form) | 0.10 |
| L-Pyroglutamate | 14.9 |
| DL-Pyroglutamate | 14.7 |

Example 19 Pre-Clinical Study with Vortioxetine Salts in Enteric Coated Formulations in Dogs Two different enteric coated vortioxetine formulations were compared to the commercial IR tablet and a solution of vortioxetine. The first enteric coated formulation comprised vortioxetine HBr, released at pH above 5.5 and was prepared as indicated in Example 17. The second enteric coated formulation comprised vortioxetine (DL)-pyroglutamate α-form with a core composition as indicated below

| Dose (mg) | 1 |
|---|---|
| Tablet mass (mg) | 15 |

| | % w/w |
|---|---|
| Vortioxetine puroglutamate | 9.55 |
| Microcrystalline cellulose | 86.45 |
| Croscarmellose sodium | 3.0 |
| Magnesium stearate | 1.0 |
| Sum | 100 |

The tablet cores were prepared by direct compression. A pre-blend was prepared by mixing vortioxetine pyroglutamate with microcrystalline cellulose in a 1:1 ratio. The remaining microcrystalline cellulose and croscarmellose sodium were added in a blender. Finally, magnesium stearate was added. Tablet cores were pressed using 3 mm punches.

The core tablets were sub-coated with Opadry Pink (20% w/w) before coating with Eudragite L30 D-55 to achieve a release pH above 5.5. Coating suspensions are indicated below

| % w/w | Opadry | L 30 D-55 |
|---|---|---|
| Eudragit L 30 D-55 | | 57.9 |
| Opadry Pink | 15 | |
| Triethyl citrate | | 0.9 |

-continued

| % w/w | Opadry | L 30 D-55 |
|---|---|---|
| PlasAcryl T20 | | 8.7 |
| Water | 85 | 32.5 |
| Total (%) | 100 | 100 |

The protocol used for the dog in vive studies was approved by the institutional ethics committee in accordance with Danish law regulating experiments on animals and in compliance with EU directive 2010/63/EU, and the NIH guidelines on animal welfare. Male beagle dogs was used for the in a non-randomised cross-over design, with an average weight of 9.23-11.2 kg. The animals was fed twice daily with approximately 240 grams of Certified Dog Diet daily (Beijing Vital Keao Feed Co., Ltd. Beijing, P. R. China) and kept in rooms with controlled and monitored for relative humidity (40% to 70% RH) and temperature from 18° C. to 26° with 10 to 20 air changes/hour. The room was on a 12-hour light/dark cycle except when interruptions were necessitated by study activities.

Before administration of the formulations the animals was be fed the afternoon (at 3:30 to 4:00 pm) prior to the day of dosing and the remaining food was removed in the morning. Food was withheld until 10-hour post-dose. The animals had free access to drinking water through-out the study. 30 min before administration of the oral formulation the animals was injected intramuscular with 6 μg/kg of pentagastrin in a saline solution. The animals were administered per orally with 20 mg vortioxitine as either of the three tablets or an oral solution containing 1 mg/mL of vortioxitin solubilized in 5% 2-hydroxypropyl-β-cyclodextrin. Immediately following capsule/tablet administration, water was given to the mouth to the animals at the dose volume of about 10 mL/animal to help capsule swallowing.

Blood samples were collected following oral administration vortioxetine at pre-dose, 5, 15, and 30 min as well as after 1, 2, 4, 6, 8, 12 and 24 hours for analysis of vortioxetine levels in plasma. The plasma concentration-time profiles are depicted in FIG. 14, and the table below gives the mean pharmacokinetic data.

| | 20 mg HBr IR N = 4 | 20 mg HBr EC N = 4 | 20 mg pyroglutamate EC N = 4 | 20 mg HBr oral solution N = 4 |
|---|---|---|---|---|
| $AUC_{0-24\,h}$ (ng h/ml) | 553 | 245 | 481 | 631 |
| $C_{max}$ (ng/ml) | 49.9 | 19.4 | 45.5 | 58.6 |

Relevant statistical data are shown in the table below:

| Parameter | Comparison (Test v Reference) | Ratio and 90% CI of the Ratio (Test:Reference) |
|---|---|---|
| $AUC_{0-72\,h}$ (ng h/ml) | 20 mg IR v 20 mg HBr EC | 0.44 (0.30, 0.65) |
| | 20 mg IR v 20 mg pyroglutamate EC | 0.83 (0.65, 1.06) |
| | 20 mg IR v 20 mg solution | 1.17 (1.05, 1.30) |
| $C_{max}$ (ng/ml) | 20 mg IR v 20 mg HBr EC | 0.39 (0.34, 0.45) |
| | 20 mg IR v 20 mg pyroglutamate EC | 0.84 (0.51, 1.37) |
| | 20 mg IR v 20 mg solution | 1.16 (0.92, 1.44) |

The invention claimed is:

1. A vortioxetine pyroglutamate compound.

2. The compound according to claim 1, wherein the compound is selected from the group consisting of vortioxetine (L)-pyroglutamate, vortioxetine (D)-pyroglutamate and vortioxetine (DL)-pyroglutamate.

3. A pharmaceutical composition, comprising the compound of claim 1 together with at least one pharmaceutically acceptable carrier or diluent.

4. A gelable pharmaceutical composition, comprising the compound of claim 1 and a salt.

5. A gel, comprising the compound of claim 1, a salt and water.

6. A solid pharmaceutical composition for oral administration, comprising the compound of claim 1 and an enteric coating.

7. A method for preparing a gel, said method comprising mixing the compound of claim 1, a salt and an aqueous solution.

8. A method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount of the compound of claim 1 to a patient in need thereof.

9. A method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount of a gel comprising the compound of claim 1, a salt and water, to a patient in need thereof.

10. A method for the treatment of a disease selected from major depressive disorder; major depressive episode; general anxiety disorder; obsessive compulsive disorder (OCD), panic disorder; post traumatic stress disorder; cognitive impairment; mild cognitive impairment (MCI); cognitive impairment associated with Alzheimer's disease, depression, schizophrenia (CIAS); and attention deficit hyperactivity disorder (ADHD), the method comprising the administration of a therapeutically effective amount of a gel to a patient in need thereof, wherein said gel is prepared by mixing the compound of claim 1, a salt and water.

* * * * *